United States Patent [19]
Hamada et al.

[11] Patent Number: 5,493,594
[45] Date of Patent: Feb. 20, 1996

[54] METHOD AND APPARATUS FOR INSPECTION OF SOLDER JOINTS BY X-RAY FLUOROSCOPIC IMAGING

[75] Inventors: Toshimitsu Hamada, Yokohama; Kozo Nakahata, Chigasaki; Yoshifumi Morioka, Seto, all of Japan

[73] Assignee: Hitachi, Ltd., Tokyo, Japan

[21] Appl. No.: 207,796

[22] Filed: Mar. 7, 1994

Related U.S. Application Data

[63] Continuation of Ser. No. 863,500, Mar. 30, 1992, which is a continuation of Ser. No. 396,959, Aug. 22, 1989.

[30] Foreign Application Priority Data

Aug. 26, 1988 [JP] Japan ................... 63-210711
Jul. 14, 1989 [JP] Japan ................... 1-180305

[51] Int. Cl.⁶ ................................. G01N 23/02
[52] U.S. Cl. ......................... 378/34; 378/98.2
[58] Field of Search ......................... 378/58, 99

[56] References Cited

U.S. PATENT DOCUMENTS

| | | |
|---|---|---|
| 4,772,125 | 9/1988 | Toshimura et al. |
| 4,809,308 | 2/1989 | Adams et al. ............. 378/58 |
| 4,910,757 | 3/1990 | Kiyasu et al. ............. 378/58 |

FOREIGN PATENT DOCUMENTS

| | | |
|---|---|---|
| 0236001 | 9/1987 | European Pat. Off. |
| 54-143290 | 11/1979 | Japan |
| 62-219632 | 9/1987 | Japan |

OTHER PUBLICATIONS

Howard Bierman, "Packing Changes Make Automatic Testing Tougher, More Costly", from Electronics Special Report, Jul. 15, 1985, pp. 48–52.
Ronald Pound, "Image Processing Boosts the Power of Non-destructive Testing", from Electronic Packaging & Production, Jun. 1985, pp. 98–104.
Nakagawa Y., "Automatic Visual Inspection of Solder Joints on Printed Circuit Boards", SPIE Proceedings, vol. 336, Robot Vision (1982) pp. 121–127.

*Primary Examiner*—Craig E. Church
*Attorney, Agent, or Firm*—Fay, Sharpe, Beall, Fagin, Minnich & McKee

[57] ABSTRACT

A method and apparatus for inspecting a solder joint by an X-ray fluoroscopic image in which an X-ray is irradiated on an object to be inspected located by a specimen stage and having a lead of an electronic part soldered to a substrate to detect an X-ray fluoroscopic image signal, a position of a lead in a tip direction is obtained by a distribution of projection with said X-ray fluoroscopic image signal projected in a lead row direction, a position of a lead in a row direction is obtained by a distribution of projection with said X-ray fluoroscopic image projected in a lead tip direction to extract a position of a solder joint as an object to be inspected, and said X-ray fluoroscopic image is evaluated every solder joint in accordance with the postion information to effect a defect detection.

31 Claims, 27 Drawing Sheets

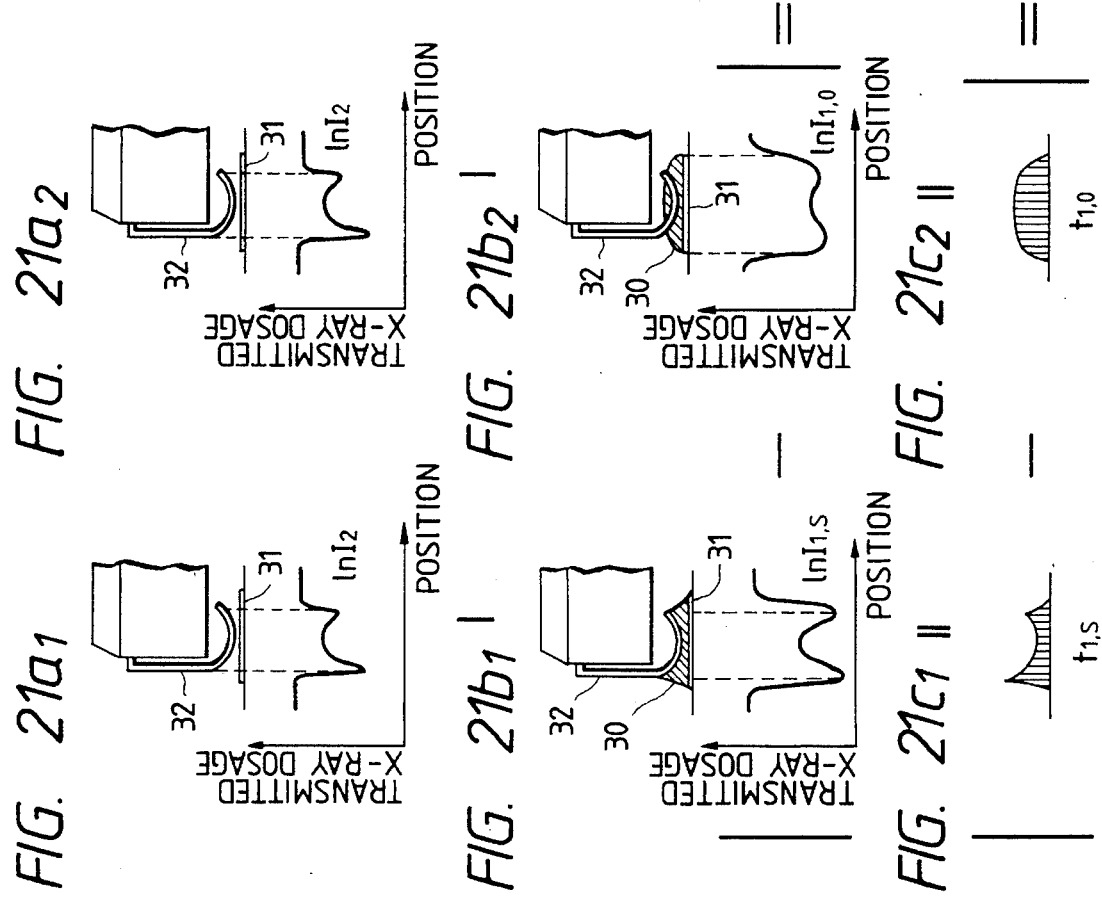

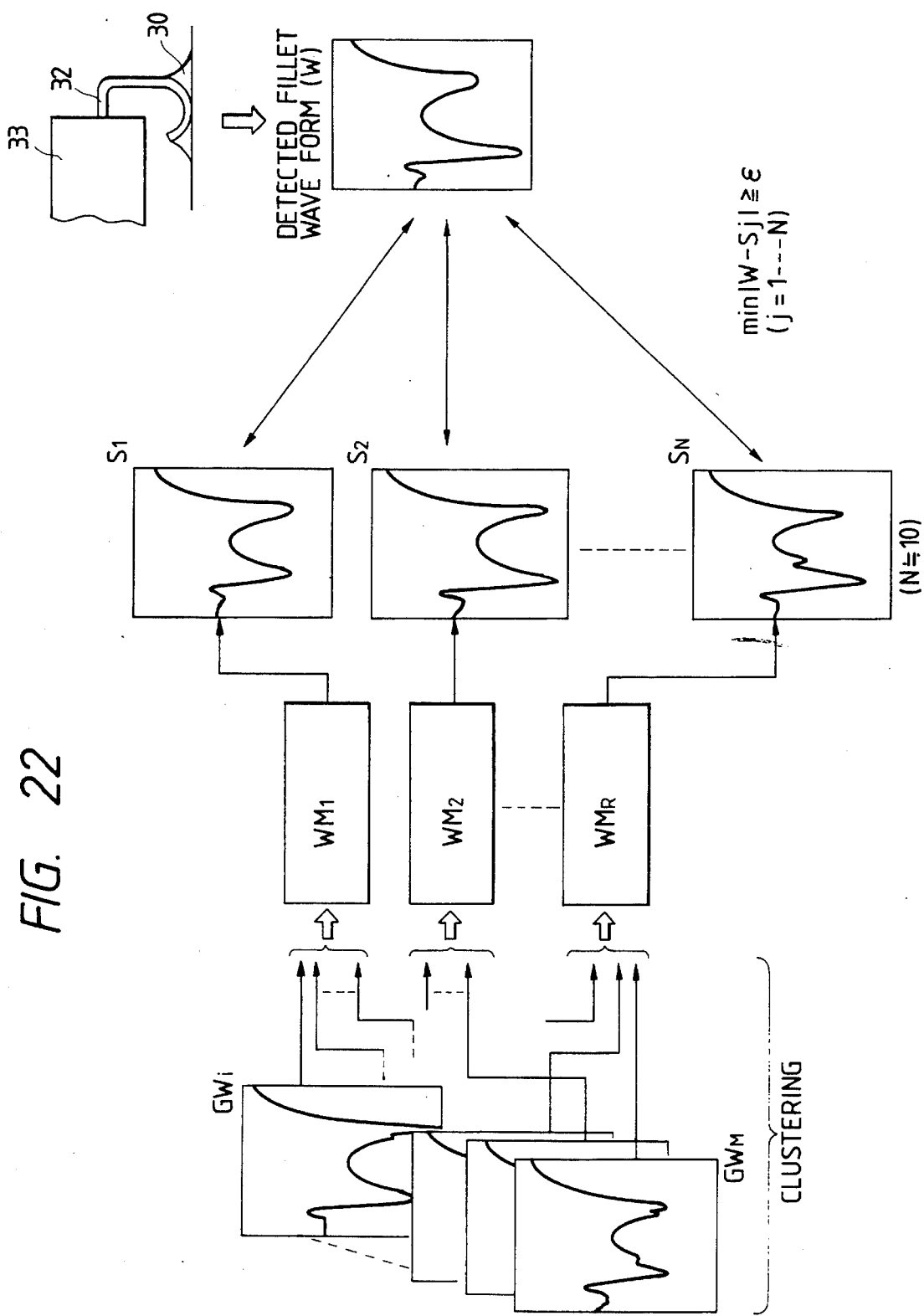

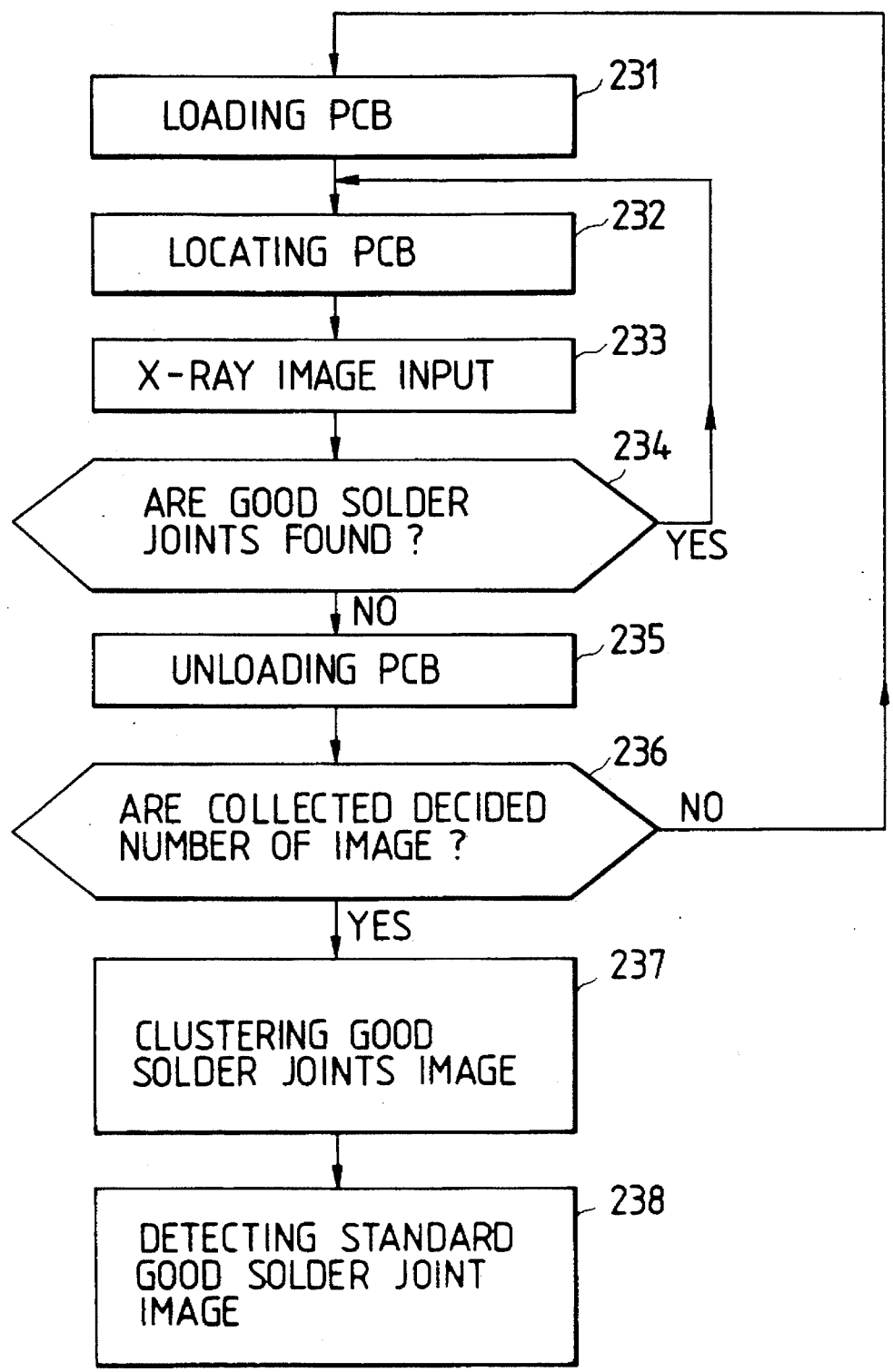

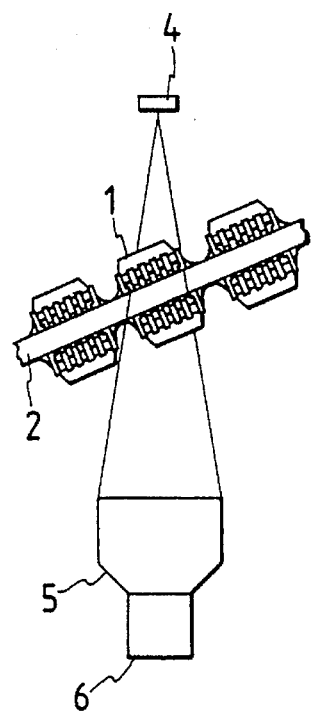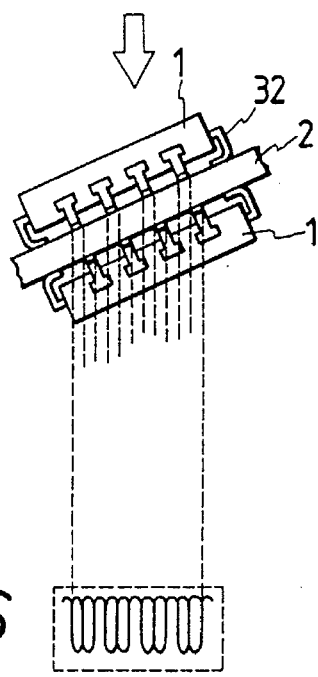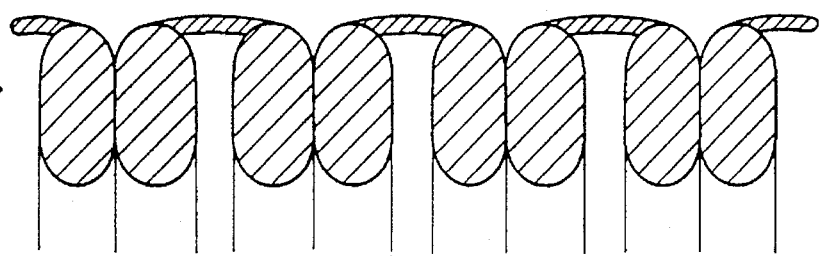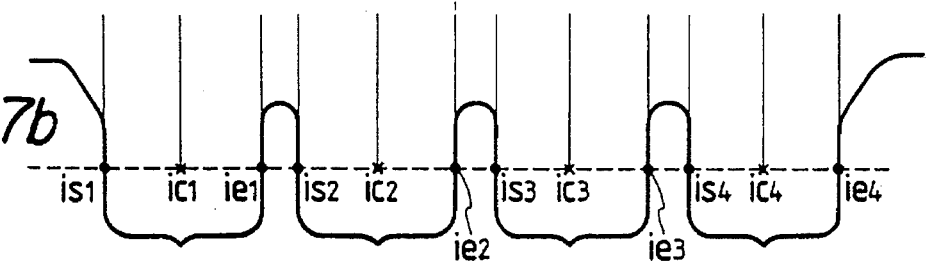

FIG. 31
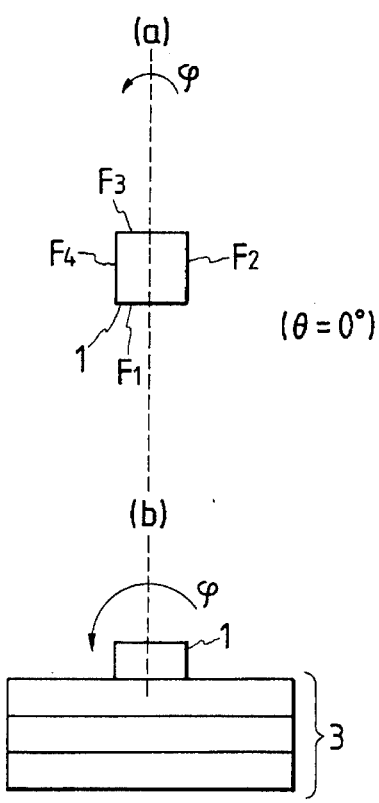
FIG. 32
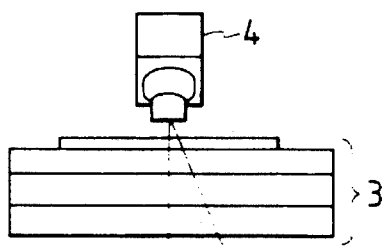
FIG. 33
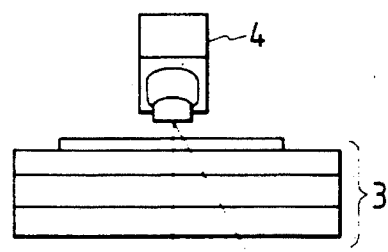
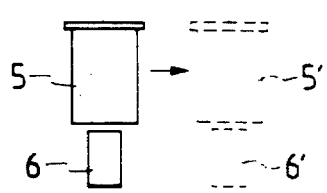
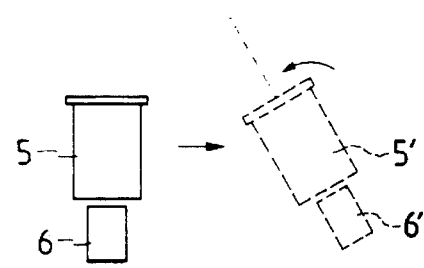

METHOD AND APPARATUS FOR INSPECTION OF SOLDER JOINTS BY X-RAY FLUOROSCOPIC IMAGING

This is a continuation of U.S. application Ser. No. 07/863,500 filed Mar. 30, 1992 which is a continuation application Ser. No. 07/396,959 filed on Aug. 22, 1989.

BACKGROUND OF THE INVENTION

This invention relates to a method and apparatus for inspection of solder joints by X-ray fluoroscopic imaging.

With recent trends toward miniaturization and increasing density of printed circuit boards, surface mounted devices have come into wide use. Correspondingly, the solder joints have been reduced in size to become a fine configuration. Soldering inspection by use of X-ray fluoroscopic imaging is described in Japanese Patent Application Laid-open Publication No. 219632/1987 (U.S. application Ser. No. 831997); ELECTRONICS/Jul. 15, 1985, pp. 48–52; and ELECTRONIC PACKAGING & PRODUCTION/June, 1985 pp. 98–104.

Regarding the wide use of surface mounted devices, the solder joints become a fine configuration as described above, and therefore, locating a solder joint to be inspected needs be done with high accuracy. However, in the above-mentioned documents, locating the solder joint is accomplished dependent upon the mechanical accuracy of a positioning apparatus. Each solder joint location being obtained by teaching the apparatus single position points. Therefore, the mechanical accuracy is affected by the accuracy of the position points taught, the pattern accuracy of the printed circuit board to be inspected, and the overall mechanical accuracy of the inspection system itself. It has been difficult therefore to detect a fine solder joint with high accuracy.

In addition, in the aforementioned documents, no consideration has been given to a dual-sided mounted board which came into wide use of late, but rather only one-sided surface mounted boards have been taken into The brightness of a transmitted X-ray image of a solder joint corresponds to the thickness of the solder joint. In the above-mentioned documents, a position of the solder joint cannot be decided with good accuracy for reasons described later, and the brightness only in a specific area within the solder joint is used as a reference value for comparison. Only the thickness of part of the solder joint is decided. Also, no consideration has been given to the quantity of solder nor the volume shape of fillers.

Moreover, if the X-ray is irradiated on a part for a long period of time, the part is damaged. However, in the prior art, no consideration has been given reduce the damage.

SUMMARY OF THE INVENTION

It is an advantage of the present invention to provide a method and apparatus for inspecting a solder joint by X-ray fluoroscopic imaging whereby the solder joint is automatically detected from a detection image signal, and on the basis of the result therefrom, the quantity of solder and the shape of the fillet can be detected for every solder joint to thereby detect a defect on a per-joint basis.

It is a further advantage of the present invention to provide a method and apparatus for inspecting a solder joint by an X-ray fluoroscopic image in which the defect decision can be made with respect to a dual-sided board similarly to a method used for one-sided boards.

It is another advantage of the present invention to provide a method and apparatus for inspecting a solder joint by an X-ray fluoroscopic image in which damage to the inspected part caused by the X-ray is reduced, without deteriorating the inspection performance.

It is a still another advantage of the present invention to provide a method and apparatus for inspection a solder joint by an X-ray fluoroscopic image in which highly accurate defect detection can be made with respect to fine solder bridges and solder balls produced between leads while removing an influence of the lead frame image (herein-after referred to as lead) on a board which J lead parts or the like are mounted.

It is another advantage of the present invention to provide a method and apparatus for inspecting a solder joint by an X-ray fluoroscopic image which can inspect and decide a deviation in mounted position of an IC lead on a circuit board, a bent or deformed lead or the like.

For achieving the aforementioned advantages, according to a first feature of the present invention, an X-ray is irradiated on an object to be inspected in which a lead of an electronic part is soldered to a substrate, the object being located by a specimen stage table to obtain a signal of the X-ray fluoroscopic image. A position of a solder joint as an object to be inspected is extracted from the X-ray fluoroscopic image, and an inspection area is defined for every solder joint in accordance with the stage table position information. The signal of the x-ray fluoroscopic image is evaluated for every inspection area to thus detect defects.

In addition, the signal of the detected X-ray fluoroscopic image is subjected to shading compensation whereby a concentration level is subjected to a logarithmic conversion, and thereafter, a projection distribution is prepared in the lead row direction and in the lead tip direction. The position of each solder joint is detected from the waveform of the projection distribution.

A fine solder joint position can thereby be automatically detected with high accuracy from the image of the X-ray fluoroscopic image of a solder joint in which an IC or the like is mounted, thus coping with the high density and miniaturized substrate (printed circuit board). Furthermore, the defect decision can be carried out with high reliability by defect detection at every solder joint.

According to a second feature of the present invention, the width or spacing betweens older joints is compared with a reference value to thereby evaluate the X-ray fluoroscopic image signal to detect defects.

According to a third feature of the present invention, every solder joint image detected is integrated to thereby calculate the quantity of solder to determine a defect.

According to a fourth feature of the present invention, a lead deviation is decided from the width in the lead row direction of the solder joint. The presence or absence of strap solder between the solder joints is decided from a binary image signal between the solder joints to determine if a defect exists.

According to a fifth feature of the present invention, a fillet shape is decided from the primary image in the lead tip direction in the central portion of the solder joint. Particularly, in the present invention, a signal of the detected X-ray fluoroscopic image is compared with image signals of a plurality of good reference images to decide wither a fillet shape is adequate. The signals of the good reference images are gathered with high accuracy. More specifically, a number of good solder joints are prepared. The solder joints are detected, and a number of primary images in the lead tip direction are extracted according to the positions thereof. Several typical waveforms are selected by a clustering process from signals of a number of primary images (waveforms) thus obtained to set the good reference images.

The signals of the good solder joints serving as a reference are automatically selected, and signals of a plurality of good solder joints corresponding to soldering variations can be easily prepared. The defect decision based on the fillet shape can thereby be carried out with high reliability.

According to a sixth feature of the present invention, the normally vertical direction of the substrate having solder joints on the inside and outside thereof is inclined with respect to an optical axis of the X-ray detection system so that signals of the X-ray fluoroscopic image of the inside and outside solder joints are not superimposed so as to detect both the inside and outside signals of the X-ray fluoroscopic image. The solder joints in the inside and outside of the substrate can thereby be separated and detected. The solder joints can be detected without being affected by the deterioration of a dynamic range detected, an the inside and outside solder joints can be inspected with high accuracy.

The inspection apparatus according to the present invention is provided with a shutter mechanism for blocking off the X-rays irradiated on ICs mounted on the substrate and a filter means for changing the distribution of the waveform of the irradiated X-rays, whereby the quantity of irradiation of X-rays to the IC can be reduced to prevent damage thereto.

A portion between IC leads is divided into a plurality of decision areas according to the presence or absence of a lead image and the type of lead image of the IC. In an area where no lead image is present, the image of a solder bridge is obtained at a darker level that the material of a printed circuit board. According to the embodiment of the present invention, a threshold lead which separates the solder from the material portion to actualize only the solder bridge is used to form a binary image and decide the presence or absence of the solder bridge. On the other hand, in an area which a plate-like lead image is detected, paying attention to the fact that a solder image is detected at a darker level than the lead image, a threshold lead which actualizes a level below a lead frame image lead is used to form the binary image, and the presence or absence of a solder bridge defect or a solder ball defect is decided. Furthermore, in an area in which a wiring pattern of a lead is to be detected a threshold lead, which separates from a material portion of a printed board, and a solder image lead as well a lead level are simultaneously actualized, is used to form the binary image. The number of patterns is obtained from the binary image signal. Then, decision of coincidence and non-coincidence with respect to the number of good reference patterns obtained in advance in a similar manner is effected. Thereby, even if a fine soldering bridge or a soldering ball having a smaller contrast than a lead image is mixed with a lead image, decision can be made in the form of non-coincidence with the number of binary image patterns, thus enabling an inspection with high sensitivity.

Employment of such an inspection method as described above, makes it possible to detect and decide with high sensitivity a fine solder having a thickness less than a lead from an image such as a bridge image superimposed over a lead image of an IC and detected, enabling a high detection performance.

Moreover, by paying attention to a partial image of a pad of a solder joint detected as a relatively dark shade image in an area externally of a tip portion of an IC lead image on the X-ray image, an image projection distribution (addition) in that area is obtained, and a pad position of the solder joint is detected from said distribution. And a decision area is defined between the pads on the X-ray image on the basis of the result of detected position of the pad, an evaluation of the binary image distribution with respect to the IC lead image forced into decision area is effected, on the basis of which a decision of deviation in position of the IC lead is effected.

As an alternative method in connection with the setting (defining) of an area for deciding a deviation of the lead, a reference position recognition pattern is provided in advance on an inspection circuit board, and a decision area is set between pads of a solder joint on the basis of the result of recognition of a position of the X-ray image with respect to said pattern. Or, this recognition of the reference position may be effected by paying attention to a clearance pattern or the like detected as a high contrast pattern on the X-ray image of the circuit board to achieve the aforesaid objective.

By employment of the above-described inspection method, the quantitative detection of a deviation amount of an IC lead with respect to a solder pad on the circuit board becomes possible. It also becomes possible to decide a deviation in position of lead and a bend of the lead with high accuracy.

Figure 24A:
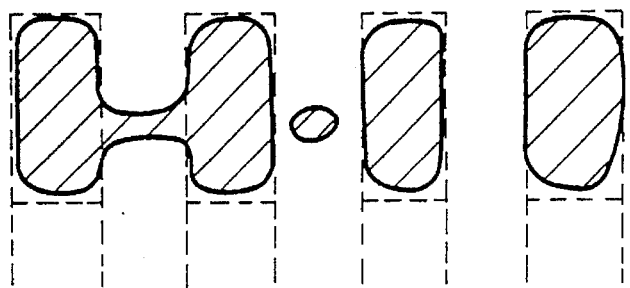
Figure 24B:
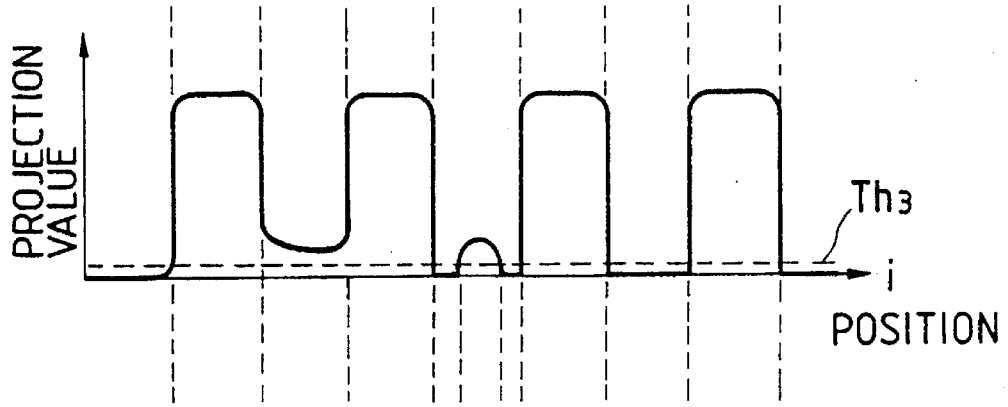
Figure 24C:
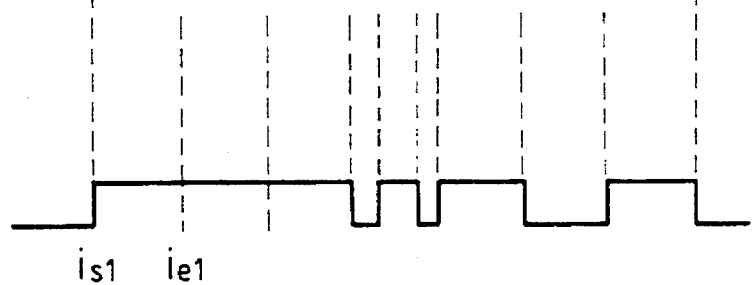
Figure 28:
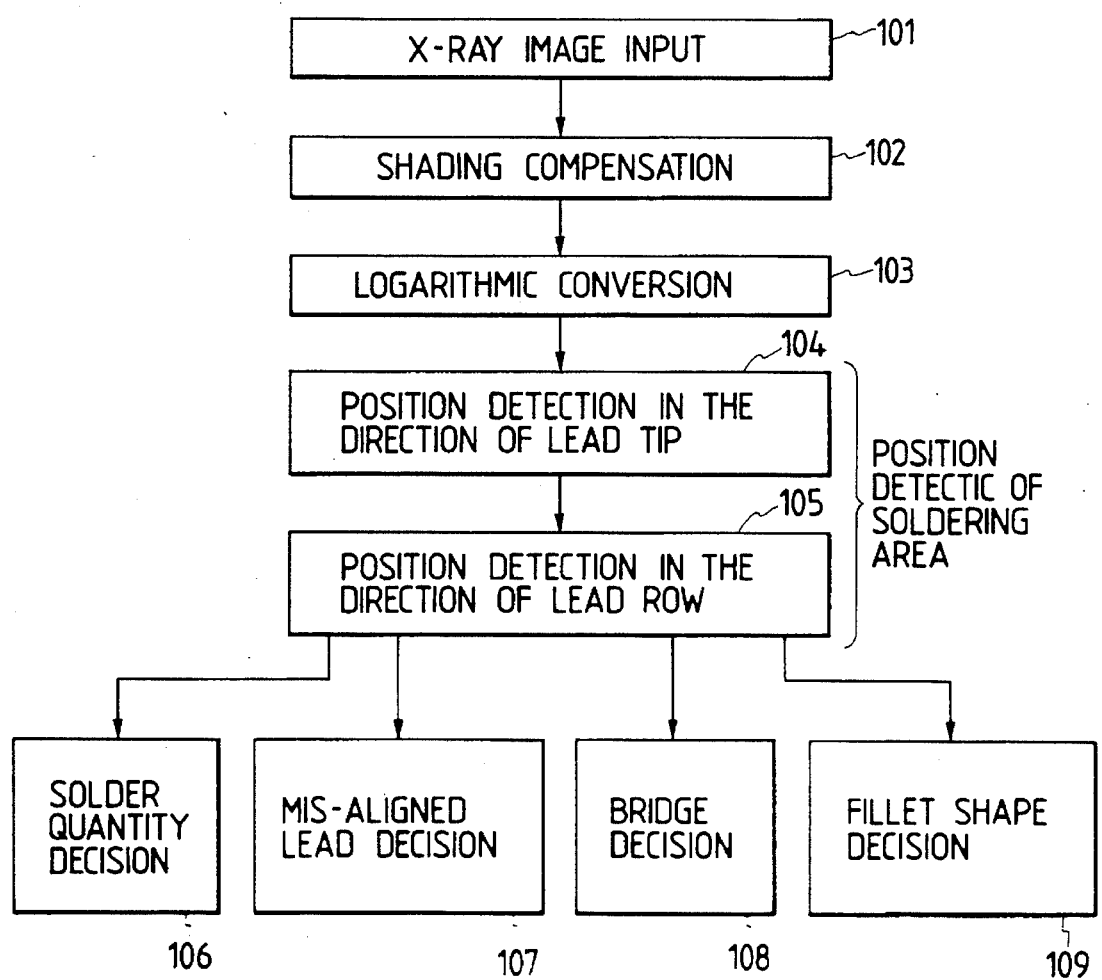
Figure 29:
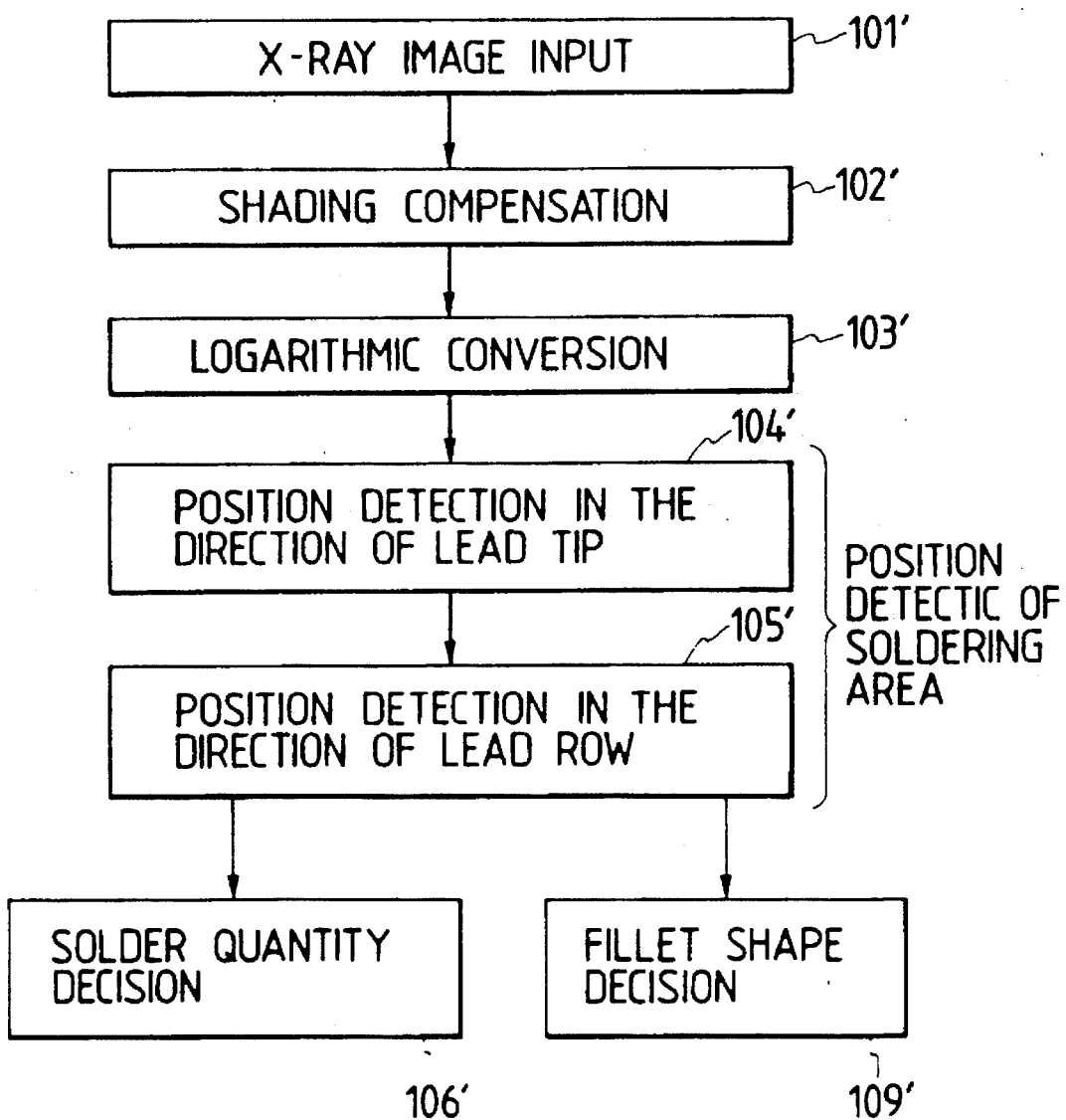
Figure 30:
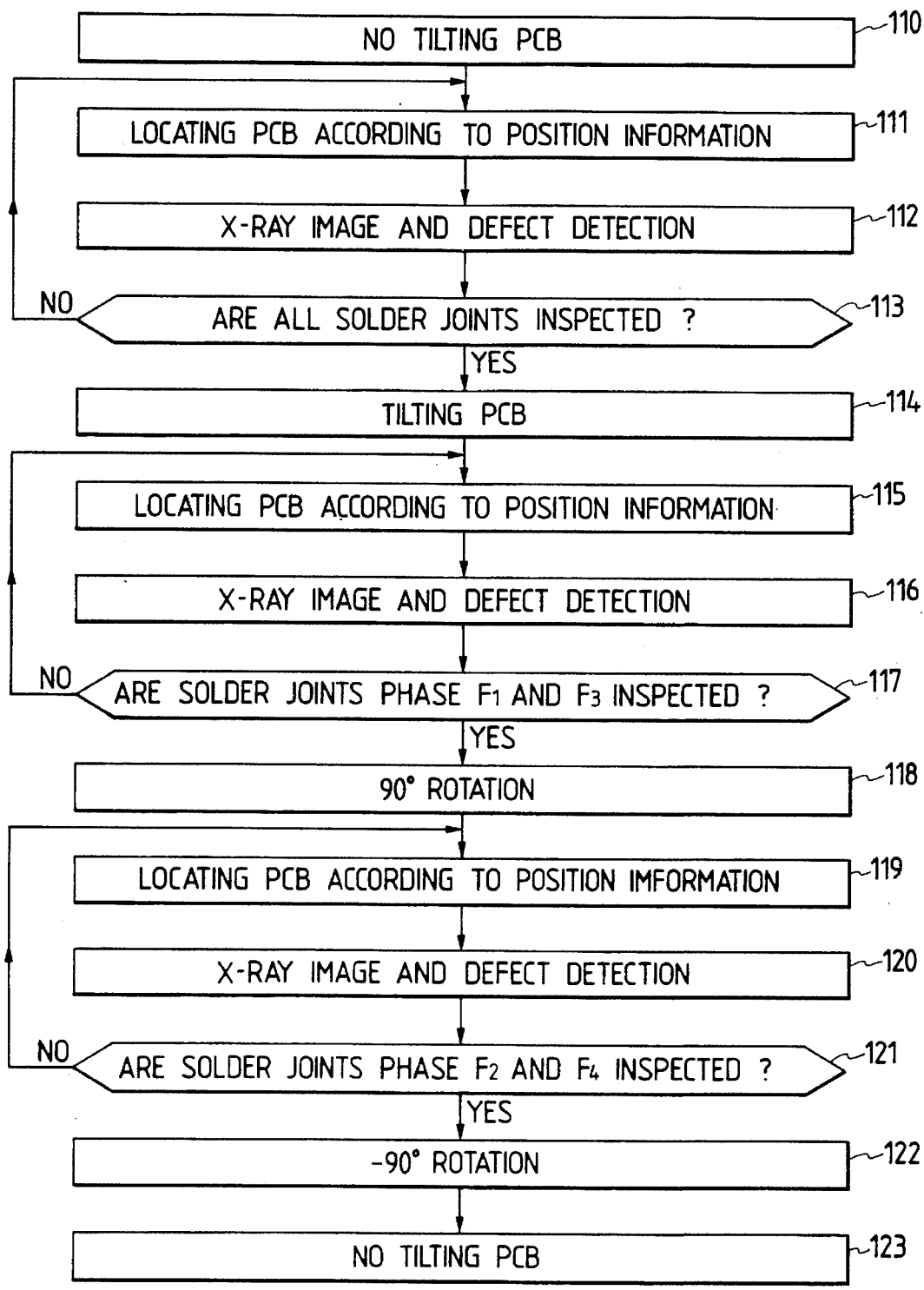
Figure 34:
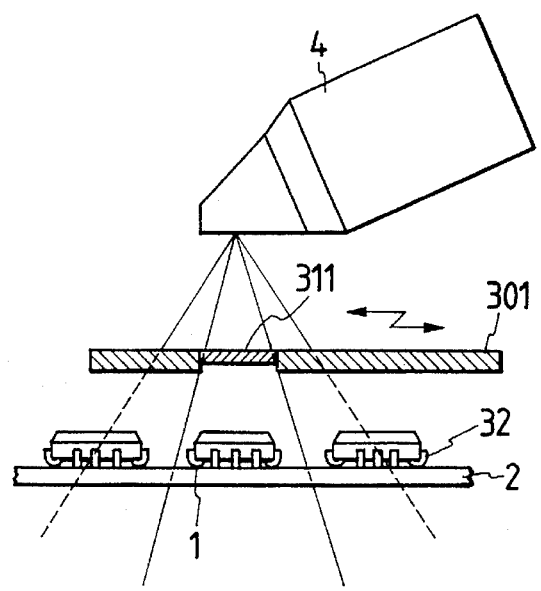
Figure 35:
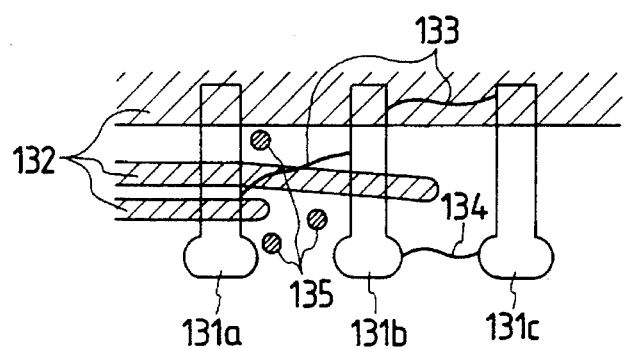
Figure 36:
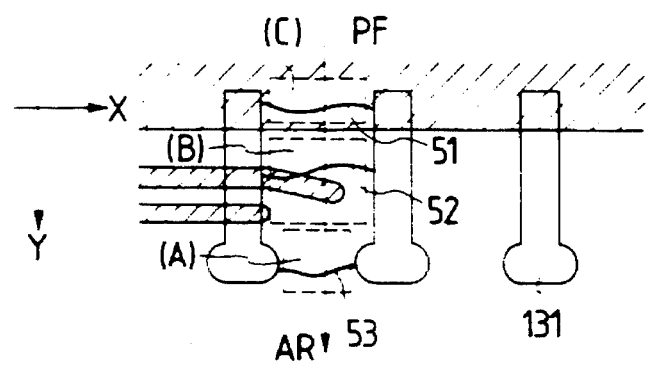
Figure 37:
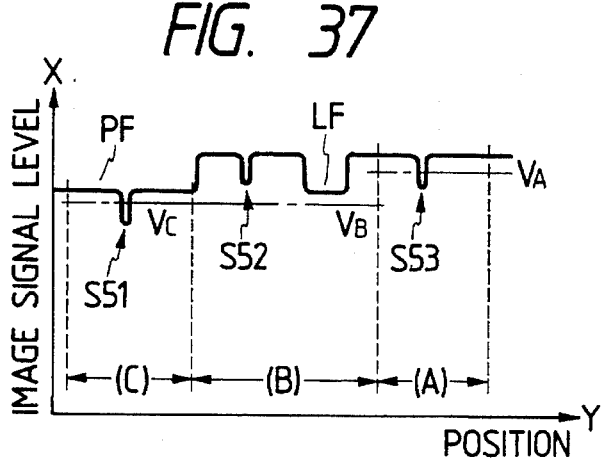
Figure 38:
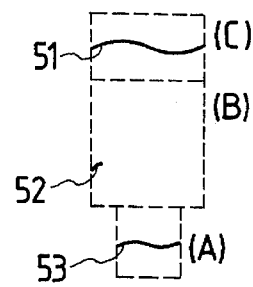
Figure 39A:
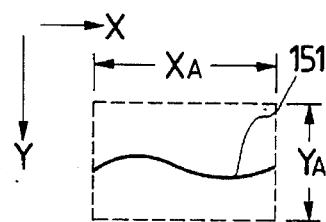
Figure 40A:
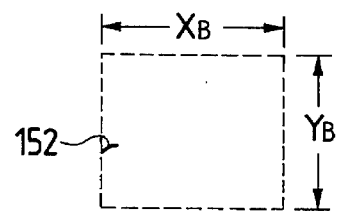
Figure 39B:
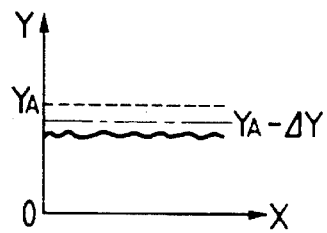
Figure 40B:
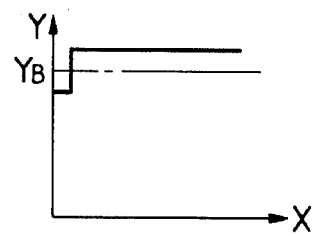
Figure 39C:
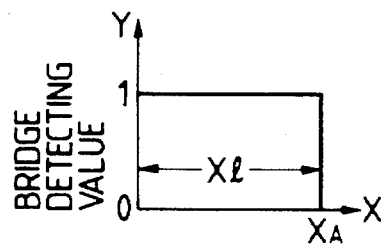
Figure 40C:
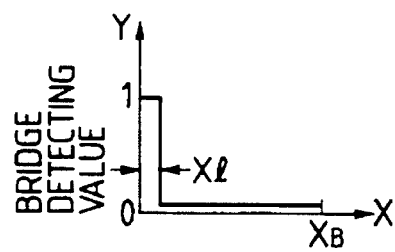
Figure 41:
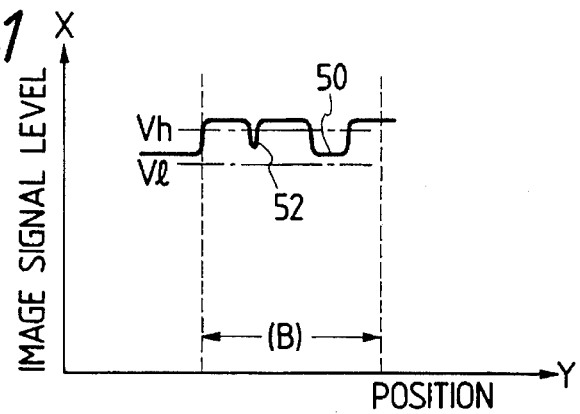
Figure 43A:
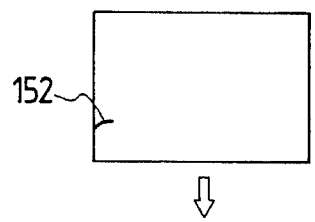
Figure 44:
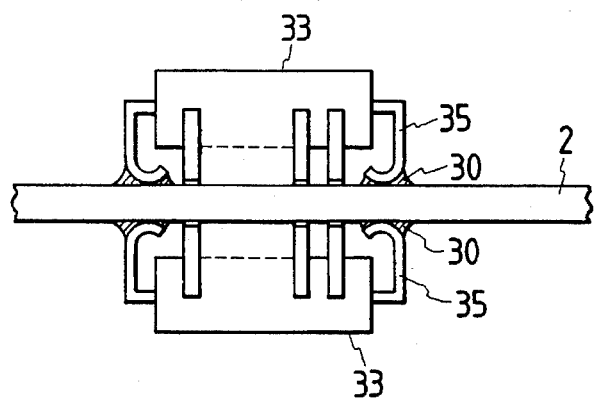
Figure 45:
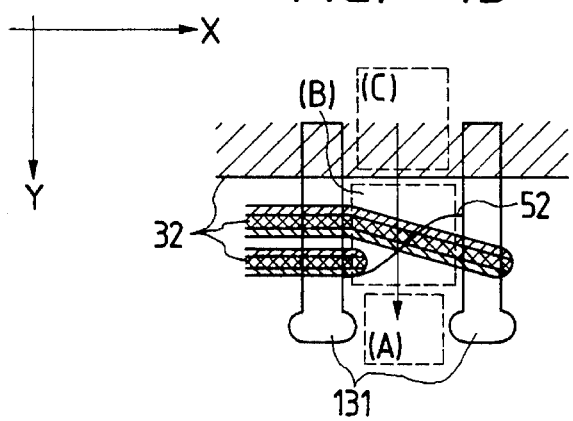
Figure 46:
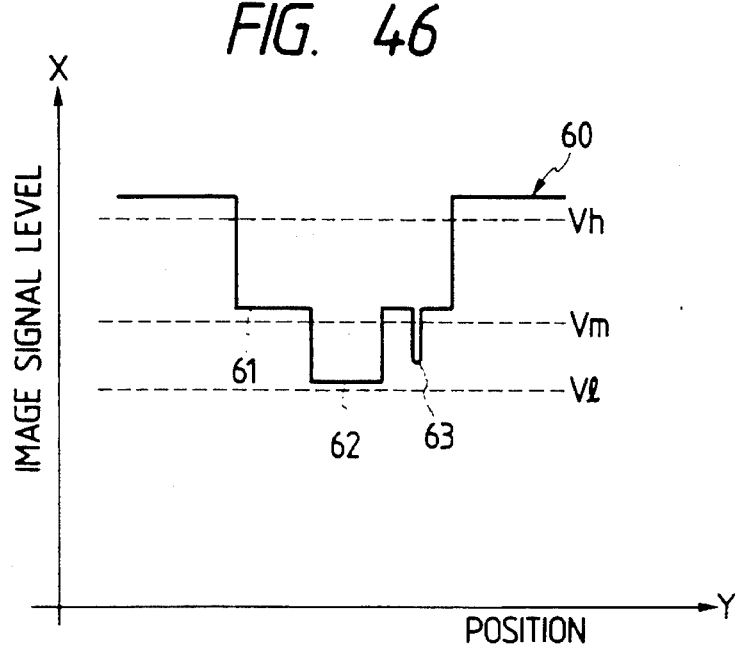
Figure 50A:
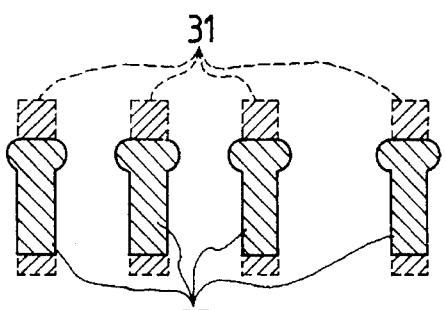
Figure 50B:
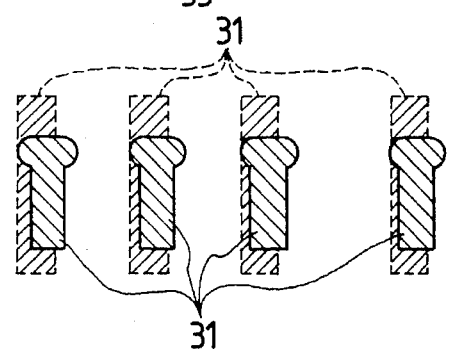
Figure 50C:
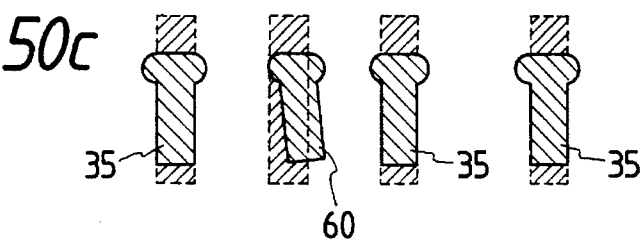
Figure 51A:
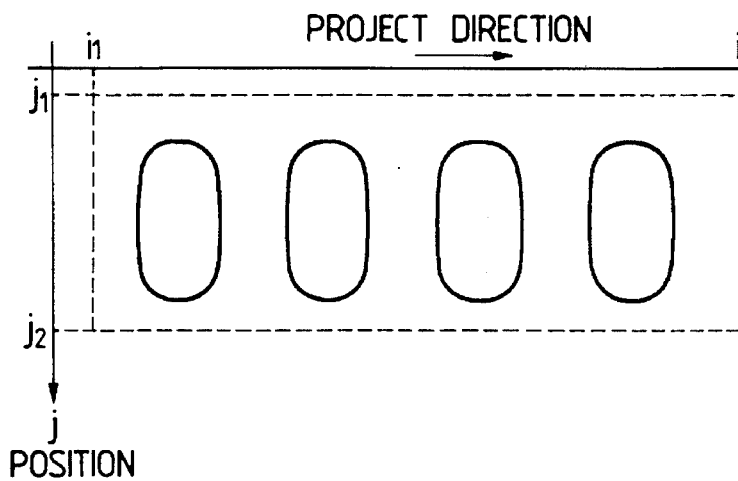
Figure 51B:
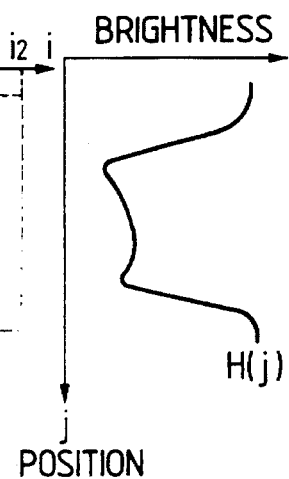
Figure 52:
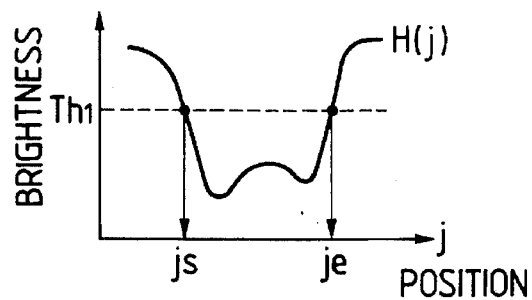
Figure 53A:
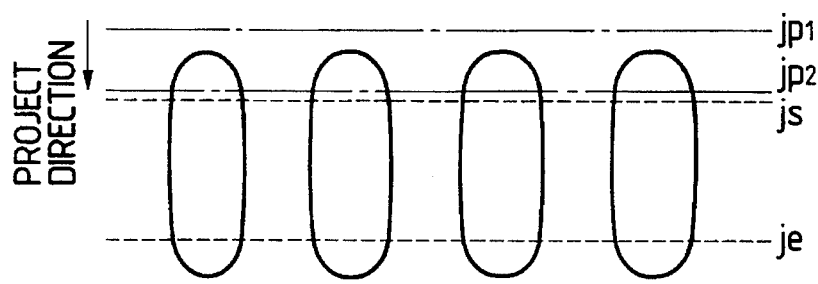
Figure 53B:
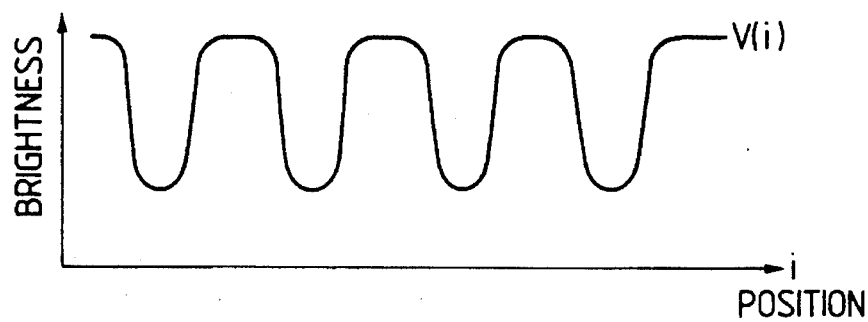
Figure 54:
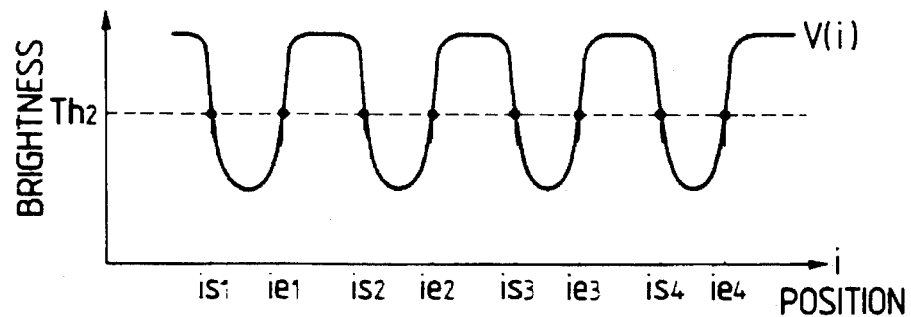
Figure 55A:
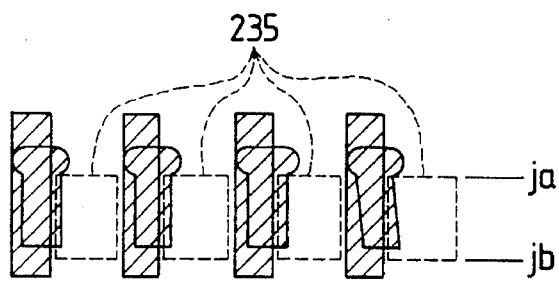
Figure 55B:
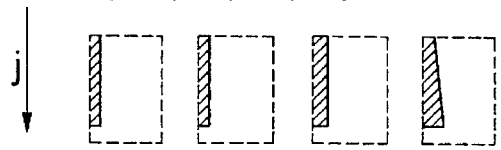
Figure 55C:
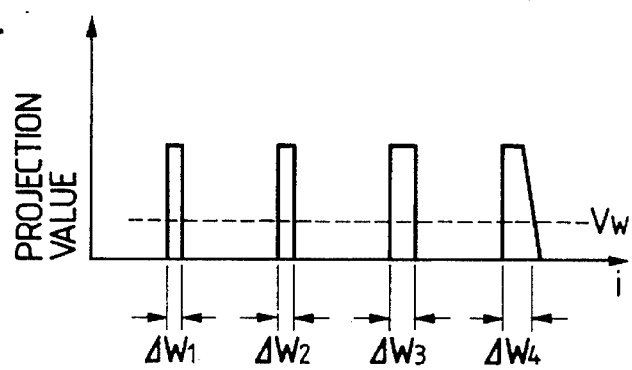
Figure 56:
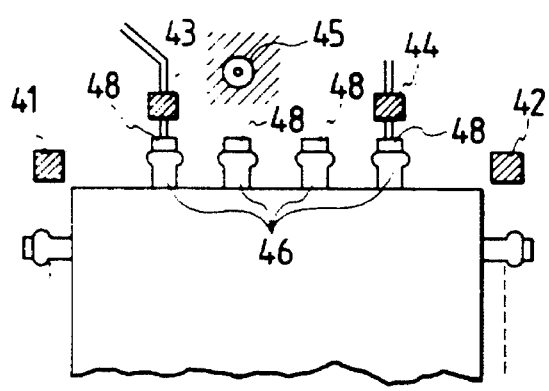
Figure 57A:
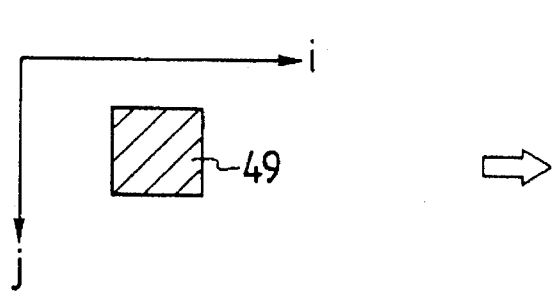
Figure 57C:
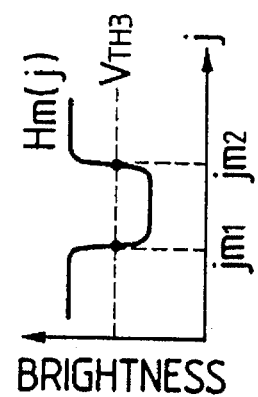
Figure 57B:
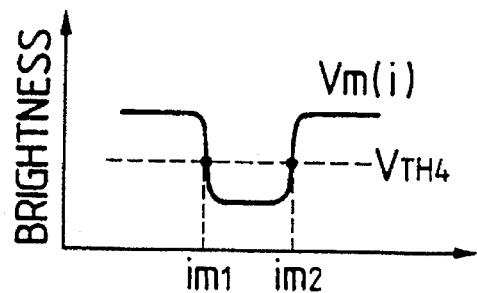
Figure 58:
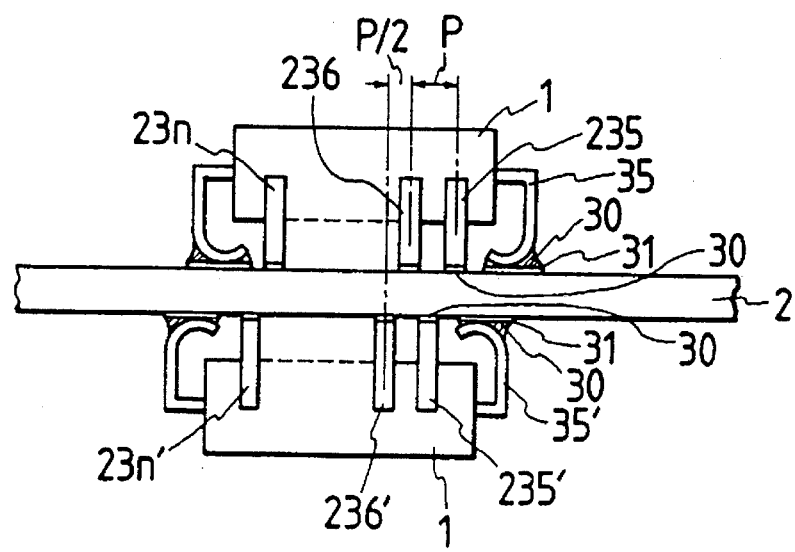

FIGS. $21a_1$ to $21c_4$ are views showing a J lead fillet shape in the case where solder is short, and in the case where there is normal solder;

FIG. 22 is a view showing a typical good fillet waveform obtained by clustering a number of good fillet waveforms;

FIG. 23 is a flowchart showing a flow for setting a reference good image;

FIGS. 24a–24c are views showing an X-ray fluoroscopic binary image when a solder ball and a solder bridge are present, a projection distribution thereof, and a binary waveform with the projection distribution binarized by a threshold $Th_3$;

FIG. 25 is a view showing the manner in which a printed board is inclined in a lead row direction to detect an X-ray fluoroscopic image;

FIG. 26 is a view showing an X-ray fluoroscopic image detected by removing an overlap of a solder joint in the manner of FIG. 25;

FIGS. 27a, and 27b are views showing the X-ray fluoroscopic image shown in FIG. 26 in an enlarged scale and a distribution of vertical projection in the lead tip direction;

FIG. 28 is a flowchart showing a flow of the image processing when the substrate is not inclined;

FIG. 29 is a flowchart showing a flow of image processing when the substrate if inclined;

FIG. 30 is a flowchart showing an inspection flow of a dual mounted (two-sided) substrate;

FIG. 31a is a plan view and 32b is a front view showing clockwise faces $F_1$–$F_4$ of IC to be inspected;

FIGS. 32 and 33 are views of an image intensifier in the case where the TV camera is moved to detect the X-ray fluoroscopic image with respect to a dual mounted (two-sided) substrate;

FIG. 34 is a view showing the case where a shutter is provided so as not to irradiate the X-ray on only the IC for which X-ray fluoroscopic image is detected in the solder joint;

FIG. 35 is a view showing an example of an X-ray fluoroscopic image with respect to a solder joint having a solder bridge defect, a solder ball defect and a lead;

FIG. 36 is a view showing the case where ares (A) to (C) are set to a solder joint having a defect of a solder bridge and a lead;

FIG. 37 is a view showing an X-ray fluoroscopic image on a scanning line AR shown in FIG. 36;

FIG. 38 is a view showing an image signal with only the bridge actualized in the areas (A) to (C) ;

FIGS. 39a to 39c are views of steps in a method for deciding a bridge in the area (A);

FIGS. 40a to 40c are views of steps in a method for deciding a bridge in the area (B);

FIG. 41 is a view showing the case where two kinds of binary images are prepared by use of two thresholds with respect to the area (B) where a pattern image of a lead is detected;

FIGS. 42a to 42d are views outlining a method for deciding a bridge from a binary image signal caused by a threshold Vh;

FIGS. 43a to 43d are views outlining a method for deciding a bridge from a binary image signal caused by a threshold Vl;

FIG. 44 is a cross-sectional view showing a dual mounted substrate (two-sided) to which a bridge decision can be applied;

FIG. 45 is an overhead and phantom view showing an X-ray fluoroscopic image obtained from a dual mounted substrate having a bridge defect;

FIG. 46 is a view showing the case where three thresholds Vh, Vm and Vl are provided in the area (B) in the image shown in FIG. 45 to obtain three types of binary image signals;

FIGS. 47a–47d, 48a–48d and 49a–49d are views illustrating a method for deciding a bridge from each of the three binary image signals respectively;

FIGS. 50a–50c are views showing normal and deviated J lead X-ray fluoroscopic images, respectively;

FIGS. 51a and 51b are views illustrating a method for obtaining a brightness distribution H(j) of horizontal (lead row direction) projection with respect to X-ray fluoroscopic images of the J lead shown in FIGS. 50a–50c;

FIG. 52 is a view showing the detection of positions (js, je) of a vertical solder joint from the brightness distribution H(j) of the horizontal projection;

FIGS. 53a and 53b are views showing areas jp1–jp2 moved through a predetermined amount with respect to the js and je shown in FIG. 52 and a brightness distribution V(i) of vertical projection in said areas;

FIG. 54 is a view showing a method for obtaining decision areas ($i_{sn}$–$i_{en}$) by thresholding the distribution V(i) of vertical projection with the threshold $Th_2$;

FIGS. 55a–55c are views of steps in a method for deciding a lead-deviated defect with respect to the decision ares ($i_{sn}$–$i_{en}$);

FIG. 56 is a view showing another embodiment for obtaining a lead-deviation decision area set between substrate pads;

FIG. 57 is a view for obtaining distributions Hm(j) Vm(i) of projection in a horizontal direction and in a vertical direction with respect to position recognition reference patterns shown in FIG. 56; and FIG. 58 is a front view showing a dual mounted substrate in which ICs are arranged on both surfaces thereof with a pitch P deviated (shifted) by P/2 so that X-ray fluoroscopic images of the leads in both surfaces do not overlap.

DESCRIPTION OF THE PREFERRED EMBODIMENTS

Figure 1:
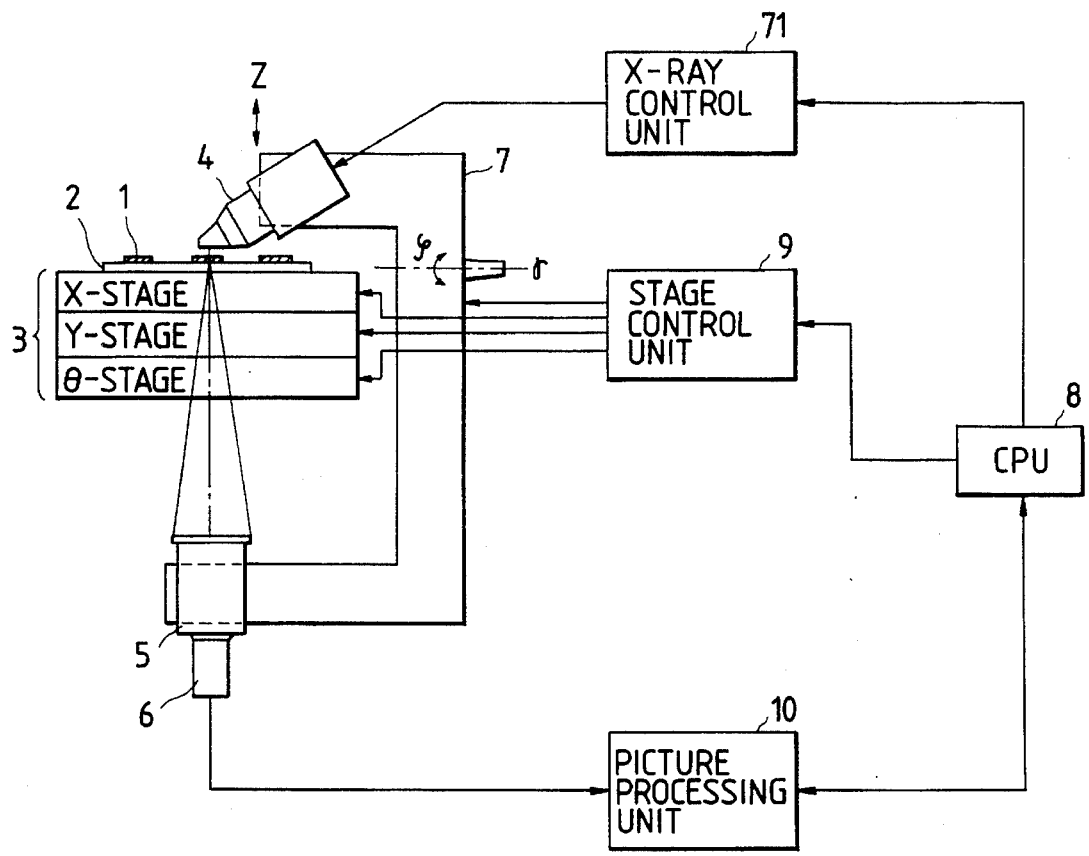
FIG. 1 is a schematic structural view showing one embodiment of apparatus for inspecting solder joints by X-ray fluoroscopic imaging.
Figure 2:
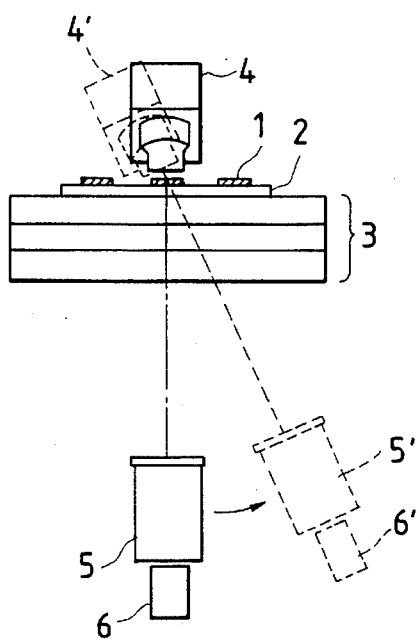
FIG. 2 is a side view showing one embodiment in which the X-ray is obliquely irradiated on the substrate, with ICs or the like mounted thereon, to detect an X-ray fluoroscopic image.

An embodiment of the present invention will be described hereinafter with reference to FIG. 1. In FIG. 1, a printed circuit board (PCB) 2 with a part 1 mounted by soldering is placed on a XYθ stage (multi-axis positioning table) composed of X, Y and θ stages. A micro-focus X-ray source 4, an image intensifier 5, such as an X-ray image detector, and a TV camera 6 are mounted on a ψ stage 7 which rotates about r in a direction of ψ. As shown in FIG. 2, the X-ray is obliquely irradiated on the PCB 2 so that a transmitted X-ray image can be detected. An X-ray control unit 71 controls voltage of the X-ray source 4, current thereof, focussing, generation of X-ray, etc., according to a command from CPU 8. The X-ray source 4 can be controlled in a direction of z. A stage control unit 9 actuates the XYθ stage 3 and the ψ stage 7 according to a command from CPU 8. A picture processing unit 10 receives a video signal from the TV camera 6, and processes an image according to a command from CPU 8. As the result, the CPU 8 decides a defect of each solder joint.

FIG. 3 shows typical examples of surface mounted parts which comprise the bulk of the objects to be inspected by the present invention. That is, FIG. 3(a) shows Gull wing lead type (SOP), FIG. 3(b) Quad Flat Package type (QFP), FIG. 3(c) Mini Square Package type (MSP) with Butt-joint lead, FIG. 3(d) Plastic Leadless Chip carrier type (PLCC) with J-lead, and FIG. 3(e) Leadless Chip type which is a lead-less type.

FIG. 4 shows a cross-section of a solder joint of each of the above-described types. FIG. 4(a) shows (SOP) or (QFP) types, FIG. 4(b) (PLCC), FIG. 4(c) (MSP), and FIG. 4(d) (LCC). In FIG. 4, reference numeral 30 designates solder, 31 a substrate pad, 32 a lead, 33 an IC package, and 35 a J lead. The lead will be generally referred to as "lead 32" except the special case, including the J lead case.

In the present invention, in order to explain how the X-ray image of the solder joint is processed and how a defect is determined, an example of J lead called PLCC (Plastic Leaded Chip Carrier) and SOF (Small Outline J-bend) will be described. As shown in the J lead of FIG. 4(b), it is difficult to determine a defect externally. This is one type of part to be inspected by the X-ray system.

FIG. 5 shows examples of defects to be inspected.

Figure 5A:
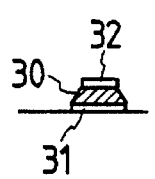
FIG. 5 is a view showing various defects in the solder joints.
Figures 5B, 5C:
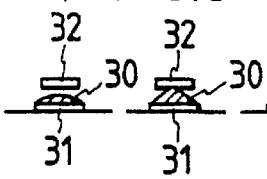
Figures 5D, 5E:
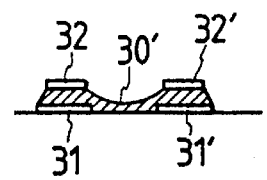

First, how defects occurring when the amount of solder is improper such as a short of solder, a surplus of solder, etc. represented by the case of small fillet as shown in FIG. 5(c), and other lifted lead, deviated lead, bridge defects, etc. are detected will be described. FIG. 5(a) shows the case of a good product, in which 30 is solder, 31 a substrate pad and 32 a lead. FIG. 5(b) shows the case where the lead 32 is a part (lifted) from the solder 30. FIG. 5(c) shows the case where a solder filet is small. FIG. 5(d) shows the case where a lead 35 is considerably deviated from the substrate pad 31. FIG. 5(e) shows the case where leads 32 and 32' adjacent to each other form a bridge by solder 30'.

Figure 6:
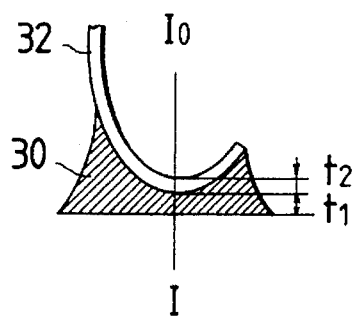
FIG. 6 is a view showing the transmitted X-ray dosage in the J. lead case.

FIG. 6 is a view for explaining the formation of a transmitted X-ray image in a J lead. Let $I_0$ be the intensity of an incident X-ray, $t_1$ be the thickness of the solder joint, $t_2$ be the thickness of those materials other than the solder, for example, the thickness of the J lead, $\mu_1$ be the X-ray absorption coefficient of solder, and $\mu_2$ be the X-ray absorption coefficient of those materials (mainly, lead and wiring pattern) other than solder. The transmitted X-ray image then is given by $$I = I_0 \exp(-\mu_1 t_1 - \mu_2 t_2) \quad (1)$$

The X-ray absorption coefficient is a constant determined by the material type and the X-ray wavelength. The X-ray absorption coefficient increases as the atomic number of the material increases (absorbs much X-rays). Since the solder joints (Pc and Sn) are larger in atomic number than other portions (Fe, Cu, etc.), the image becomes darker. If Equation (1) is subjected to a logarithmic conversion, the Equation (2) below is obtained:

$$\ln I = \ln I_0 - \mu_1 t_1 - \mu_2 t_2 \quad (2)$$

and the image after the logarithmic conversion remains unchanged.

If Equation (2) is further modified, then Equation (3) below is obtained:

$$t_1 = \frac{\ln I_0 - \ln I - \mu_2 t_2}{\mu_1} \quad (3)$$

$I_0$ and $\mu_1$ are constants, while $\mu_2$ and $t_2$ change in value according to the difference in a wiring pattern of a printed circuit board. However, the $\mu_2$ and $t_2$ values are mostly determined according to the part and the position of the solder joint since the thickness of the wiring pattern is small. If lnI is integrated over the solder joint, the value $(\Sigma t_1)$ obtained by integrating $t_1$, that is, the value corresponding to the amount of solder can be calculated. In this case, $$\Sigma t_1 = -\frac{\Sigma \ln(I/I_0) + \mu_2 \Sigma t_2}{\mu_1} \quad (4)$$

When the lead is deviated from the surface of the board, the width of the solder joint becomes widened. Thereby, a deviated lead can be extracted by calculating the width of the solder joint.

Since the solder X-ray image is darker than the other portions, it can be extracted as a binary image by binarizing it with a suitable threshold level. Thereby, the binary image is projected in the lead tip direction between the solder joints whereby defects such as a bridge, solder balls, etc., can be extracted.

The X-ray fluoroscopic image when solder is not present is obtained by use of Equation (2) as follows:

$$\ln I' = \ln I_0 - \mu_2 t_2 \quad (5)$$

From (2)–(5), we obtain:

$$t_1 = \frac{(\ln I' - \ln I)}{\mu_1} \quad (6)$$

Figure 7A:
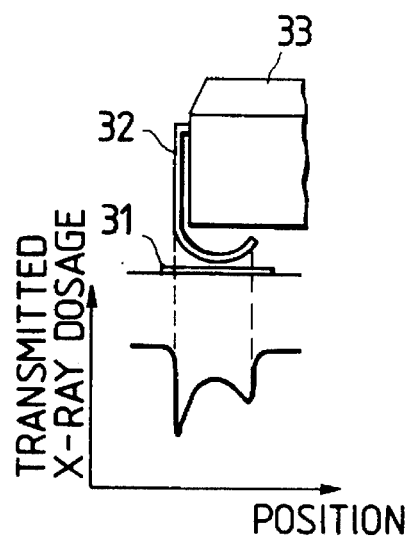
FIGS. 7a, 7b and 7c illustrate the detection of a fillet shape of a J lead.
Figure 7B:
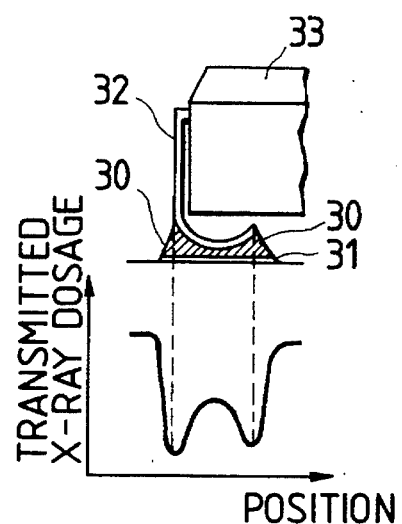
Figure 7C:

That is, a difference of an image between the case where solder is present as shown in FIG. 7a and the case where solder is absent as shown in FIG. 7b is obtained, whereby a fillet shape is shown in FIG. 7c, can be extracted as a distribution of the solder thickness $t_1$. Accordingly, in the aforementioned determination of the amount of solder, the lifted lead defect wherein the amount of solder is normal can be detected.

Figure 8:
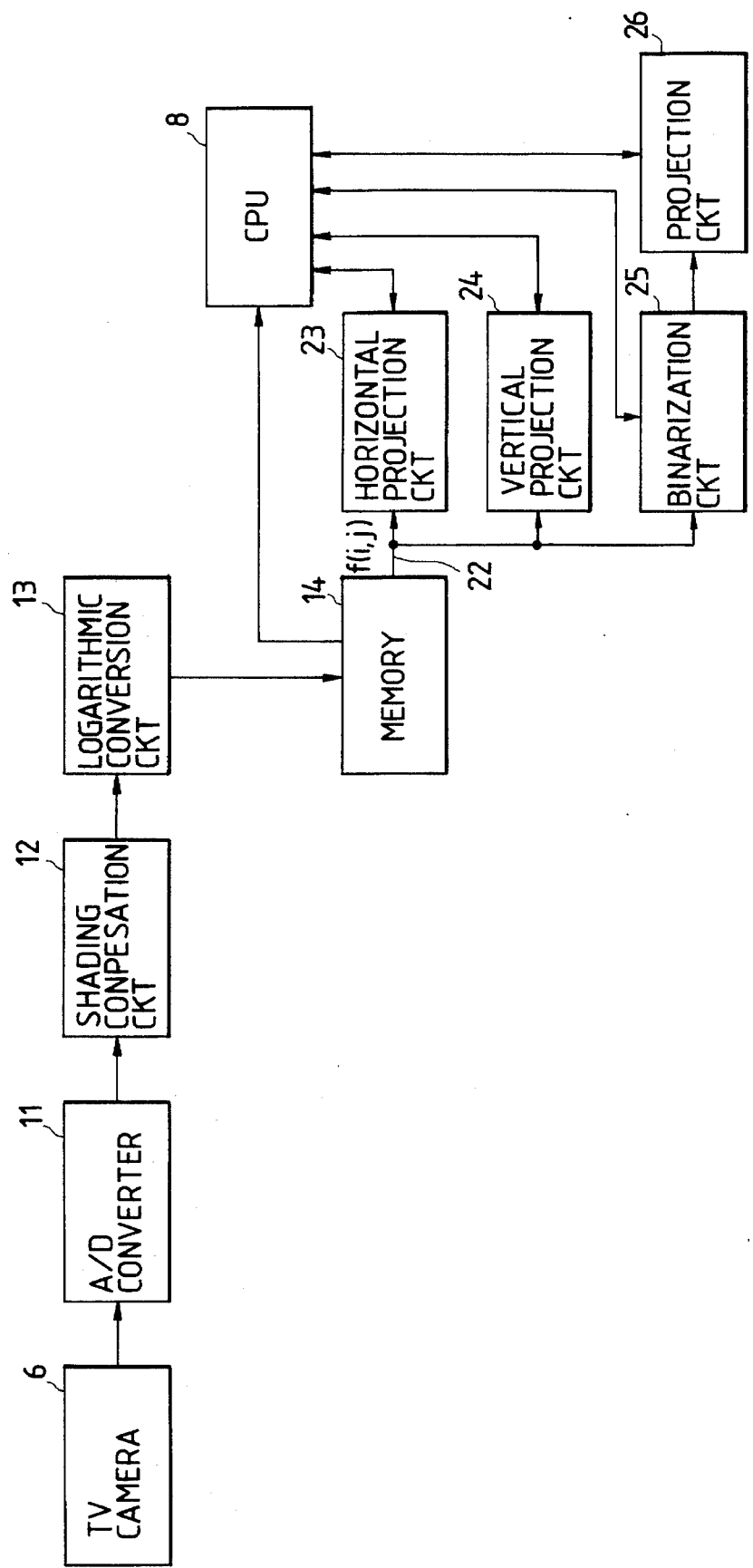
FIG. 8 is a structural block view specifically showing the picture processing unit shown in FIG. 1.

A specific structural block example of the picture processing unit 10 (shown in FIG. 1) for effecting the processing as described above is shown in FIG. 8. In FIG. 8, a video signal from a TV camera 6 is converted into a digital value by an A/D converter 11, after which it is inputted into a memory 14 through a shading compensation circuit 12 and a logarithmic conversion circuit 13. The shading compensation is to compensate for variations in video level despite the seemingly even brightness in the central portion and in the circumferential portion of a picture plane. Detecting images (called white images) W (i, j) when a material to be inspected is not present and detecting images (called black images) B (i, j) when the X-ray is not generated are used to obtain:

$$f(i, j) = \frac{g(i, j) - B(i, j)}{W(i, j) - B(i, j)} \quad (7)$$

by detecting images g (i, j). Then, the detected image is normalized with respect to the white image and black image. A specific structural example is shown in FIG. 9.

Figure 9:
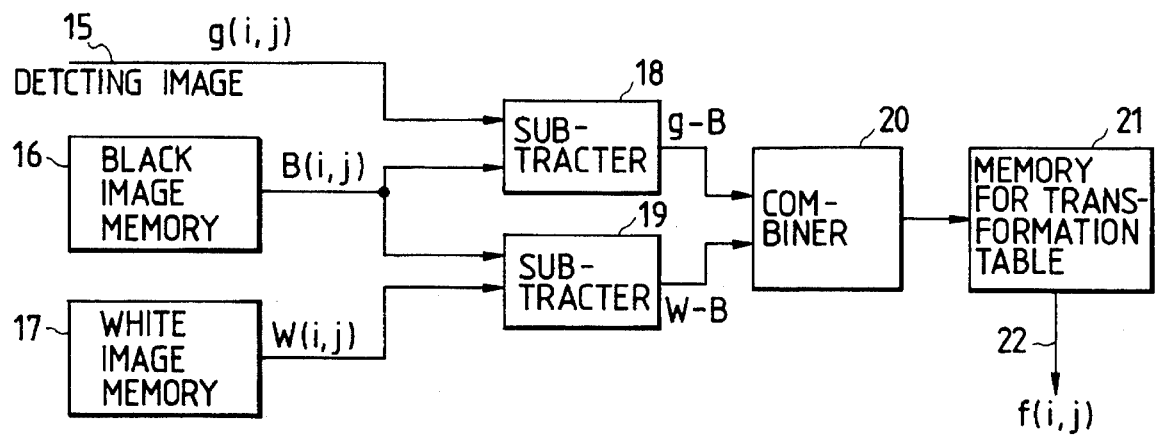
FIG. 9 is a block view showing the structure of the device for normalizing the detecting image.

In the FIG. 9, the logarithmic conversion is included, and the image after logarithmic conversion is outputted as f(i, j). In FIG. 9 a difference between a detection image signal 15, an output of a white image memory 17 and an output of a black image memory 16 is obtained by subtracters 18 and 19. Outputs are combined (g-B)(W-B) as a bit string by a combiner 20. The output of 20 is addressed to read the content of a memory 21 for transformation table 21 to output the image f(i, j) (hereinafter referred to as 22) after transformation. The content of the memory for transformation table 21 is stored upon logarithmic conversion in an address in which a value of the left side of Equation (7) is determined by a denominator and a numerator of the right side thereof.

Figure 10:
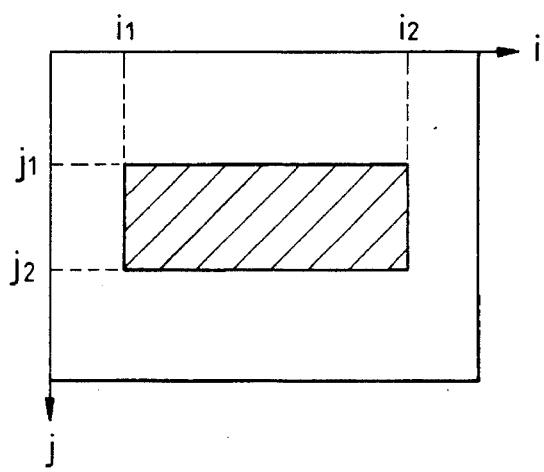
FIG. 10 is a view showing area projected toward a normalized image f (i, j)

In FIG. 8 in a horizontal projection circuit 23 and a vertical projection circuit 24, the horizontal projection H(j) and the vertical projection V(i) are obtained as below with respect to the image 22 (wherein an area projected designated by CPU 8 is an area as indicated by hatching in FIG. 10):

$$H(j) = \sum_{i=i_1}^{i_2} f(i,j)$$

$$V(i) = \sum_{j=j_1}^{j_2} f(i,j)$$

A binarization circuit 25 is designed so that a threshold level (a solder or lead portion is detected as an X-ray image to be a darker level than other portions) for extracting solder (such as bridge) or a lead present between solder joints, is designated by the CPU 8 to binarized the image stored in the memory 14. A projection circuit 26 prepares a projection in the lead tip direction with respect to the binary image in an area designated by the CPU 8.

The sequence of the inspection in this embodiment will now be described. The CPU 8 controls the stages 3 and 7 (shown in FIG. 1), locates a printed circuit board and inputs an X-ray fluoroscopic image into the memory 14 in accordance with positional information of the solder joint obtained from teaching or design information. Subsequently, the CPU 8 designates projection areas with respect to the horizontal and vertical projection circuits 23 and 24 to prepare projections, analyze projections and detect the position of the solder joint. The CPU 8 analyzes the projections obtained by the 23 and 24 and the image inputted into the memory 14 in accordance with the position of the detected solder joint to extract a defect of each solder joint. The projection of the binary image is obtained by the projection circuit 26, and defects among the solder joints are extracted by how the obtained projection is analyzed.

Figure 11:
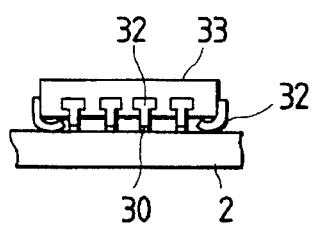
FIG. 11 is a view showing a schematic structure of one example of a J lead solder joint.
Figure 12A:
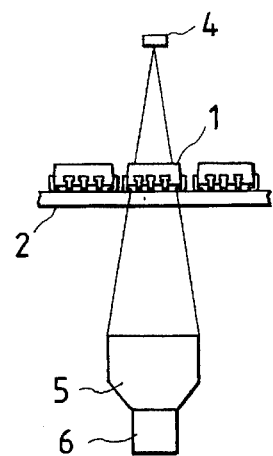
FIGS. 12a and 12b are views showing the state in which the X-ray is irradiated on the J lead solder joint shown in FIG. 11, and the X-ray fluoroscopic image obtained by a camera.
Figure 12B:
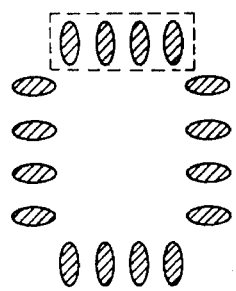
Figure 13A:
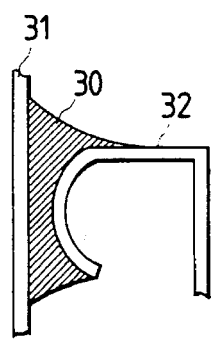
FIGS. 13a and 13b are views showing cross-section of a J lead solder joint in the lead tip direction, and the brightness of the X-ray fluoroscopic image.
Figure 13B:
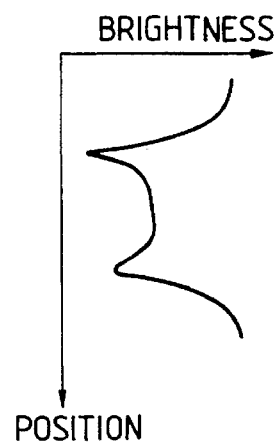
Figure 14A:
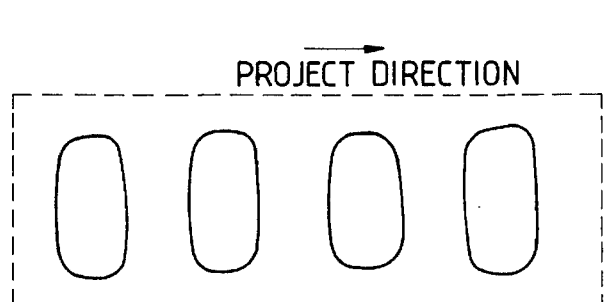
FIGS. 14a and 14b are views showing an area projected in a horizontal lead row direction and a brightness distribution H(j) of horizontal lead row projection.
Figure 14B:
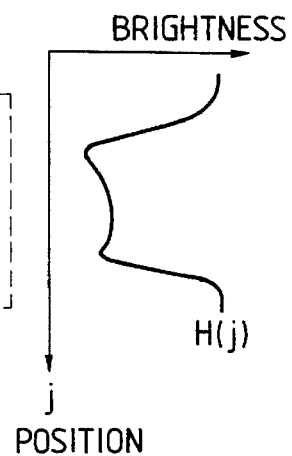
Figure 15:
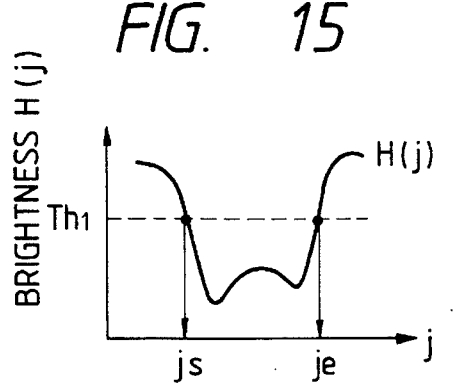
FIG. 15 illustrates the detection of positions (js~je of a vertical solder joint with a threshold $Th_1$ with respect to the brightness distribution H(j) of horizontal projection.

The aforementioned operation will be explained by way of an inspection of a J lead solder joint of the type PLCC (Plastic Leaded Chip Carrier) shown in FIG. 11. As shown in FIG. 12a, when the X-ray is irradiated, an X-ray fluoroscopic image as shown in FIG. 12b is obtained. In the following description, solder joints surrounded by the broken lines in FIG. 12b are arranged as an example. FIG. 13a shows a cross-section of a J lead solder joint, and FIG. 13b shows a variation in brightness of X-ray image in the lead tip direction. The brightness of the X-ray image decreases as the solder thickness increases. In FIG. 13b, the X-ray image becomes darkest at raised portions of the J lead. However, since the lead has a smaller X-ray absorption coefficient than does the solder, the X-ray image is darker than that of a portion where the solder thickness is maximum. When a horizontal projection is obtained by the horizontal projection circuit 23 in an area as shown in FIG. 14a with respect to the X-ray fluoroscopic image of the J lead having the features mentioned above, an additive brightness distribution H(j) signal of the horizontal projection as shown in FIG. 14b is obtained. The CPU 8 receives the H(j) signal and obtains points of intersection js and je between the threshold $Th_1$ and the brightness addition value H(j) signal as shown in FIG. 15 to set positions of the vertical solder joints. Here, the threshold $Th_1$ is set in advance, or a value is used which is subjected to interior division with a ratio wherein the maximum and minimum values of the inputted horizontal projection H(j) are set in advance.

Figure 16A:
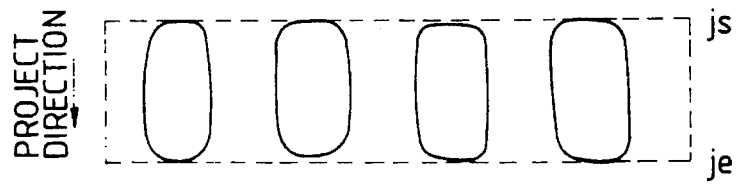
FIGS. 16a and 16b are views showing an area projected in a vertical lead tip direction and a brightness distribution V(i) of vertical projection.
Figure 16B:
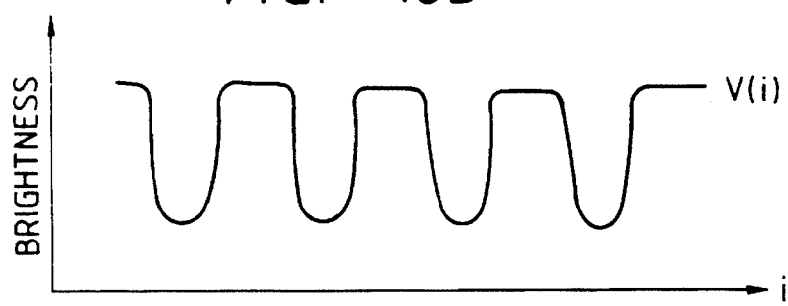

Next, when the vertical projection circuit 24 is used in the area surrounded by the dotted lines as shown in FIG. 16a with the vertical projection range being js to je to obtain the vertical projection V(i), the distribution of brightness (addition value) as shown in FIG. 16b is obtained. The CPU 8 shown in FIG. 8 inputs the vertical projection V(i) to obtain the threshold The, shown in FIG. 17, and points of intersections $is1$, $ie_1$ to $ie_4$, $is_4$ of V(i) to serve as the solder joint in the horizontal direction i. The threshold $Th_2$ is set similarly to the $Th_1$.

Figure 17:
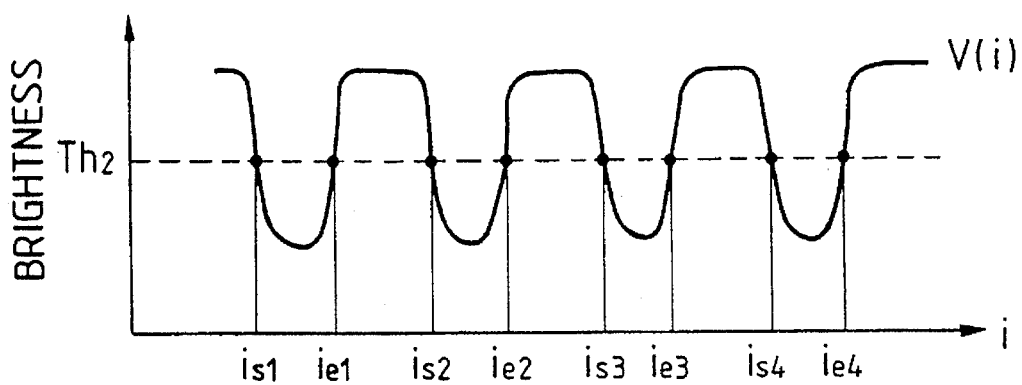
FIG. 17 illustrates the detection of positions ($i_{sn}$–$i_{en}$) of a horizontal solder joint with a threshold $Th_2$ with respect to the distribution V(i) of vertical projection.
Figure 18A:
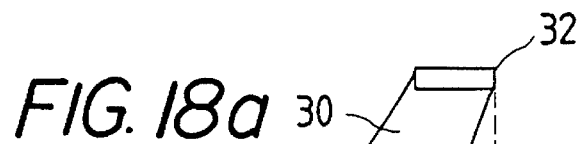
FIG. 18 is a view showing an example of a sectional shape of a lead deviation defect and its X-ray fluoroscopic image.
Figure 18B:
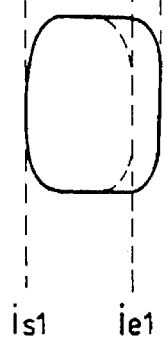

FIG. 18a shows an example of a sectional shape of a deviated lead, and (b) thereof is a plan view showing a solder joint image obtained by X-ray fluoroscopic imaging. As will be apparent also from FIG. 10, $isn$–$i_{en}$ (n=1~4) obtained in FIG. 17 are compared with a good solder joint to thereby detect a deviated lead.

As mentioned above, the X-ray fluoroscopic image has a brightness corresponding to the thickness of the various materials. Thereby, one to which image value is added corresponds to the amount of solder in the solder joint. In sections ($is_n$, $i_{en}$) (n=1~4), if V(i) is integrated, a value corresponding to the amount of solder which corresponds to each solder joint can be obtained. This can then be compared with a good solder joint to thereby extract a surplus or shortage of solder on the joint.

Figure 19:
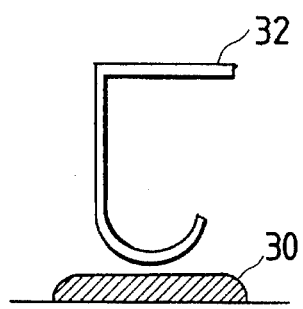
FIG. 19 is a cross-sectional view showing an example of a lifted lead defect.
Figure 20A:
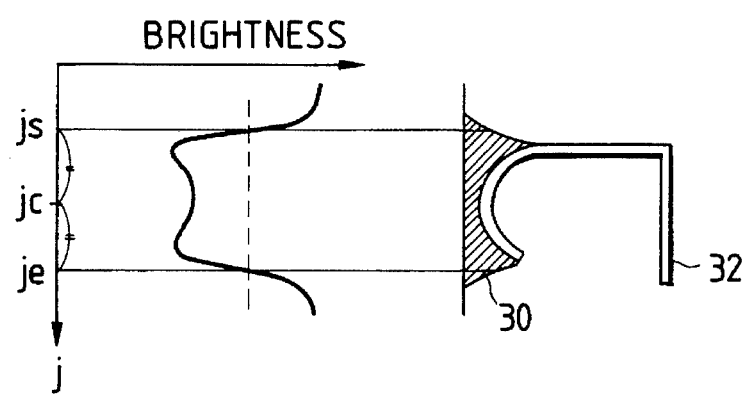
FIGS. 20a and 20b are views showing the relationship between a center position of a solder joint obtained by a good solder joint and a center position of a lead obtained with no soldering joint.
Figure 20B:
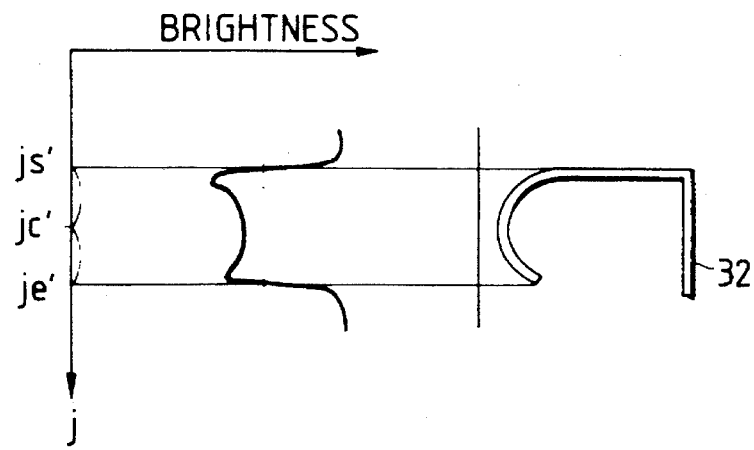

FIG. 19 shows an example of lifted lead in which the amount of solder is normal but lead is lifted. In the embodiment of the present invention, a fillet shape is first decided to detect such a defect. In order to extract a fillet's shape, the horizontal and vertical projection circuits 23 and 24, shown in FIG. 8, are used with respect to the X-ray image when solder is not present to detect a solder joint. Since the lead portion has no solder but the lead thickness is thicker than other portions and is Fe or Cu, it has a darker image value than the other portions. Therefore, as far as the lead row (arrangement) direction is concerned, substantially the same position as the good product is detected. Also with respect to the lead tip direction, as shown in FIG. 20a and 20b, a middle point jc (FIG. 20a) between positions js and je obtained in a good product and a middle point jc' (FIG. 20b) between positions js' and je' assume substantially the same position with respect to the lead. That is, if in the lead tip direction, positioning is adjusted so that jc and jc' are coincided, the lead when solder is not present can be adjusted in position to the image of an object to be inspected. An image data is inputted in advance from the memory 14 to the CPU 8 from the image without solder with jc' used as a reference at the center (position of (isk+iek)/2) in the position of the lead row direction in each solder joint. Then, a similar image data is inputted from the CPU 8 to the memory 14 in each solder joint from the image of an object to be inspected to obtain a difference from the image data without solder, whereby the fillet shape is extracted as in FIG. 21. A defect is decided by the fillet shape when a difference between a good fillet shape and a fillet shape of an object to be inspected exceeds a set value.

The decision of fillet shape will be described with reference to FIGS. $21a_1$ to $21c_4$.

Systems of FIG. $21a_1$, FIG. $21b_1$ and FIG. $21c_1$ are similar to those of FIG. 7a to FIG. 7c as previously mentioned. In this case, if a difference between an image pattern of a solderless joint shown in FIG. $21a_1$ and an image pattern of having soldered joint shown in FIG. $21b_1$ is obtained, a fillet shape shown in FIG. $21c_1$ is extracted as a distribution of the solder thickness $t_{1's}$. The joint shown in FIG. $21b$ is a good solder joint.

Next, when a solder joint of an object to be inspected subjected to decision of fillet shape is similarly processed, a fillet shape provided with a distribution of solder thickness $t_{1'0}$ is finally obtained as shown in FIG. $21a_2$, FIG. $21b_2$ and FIG. $21c_2$.

Then, if a difference between the shape $(t_{1's})$ shown in FIG. $21c_1$ and the shape $(t_{1'0})$ shown in FIG. $21c_2$ is obtained, a shape of difference $|t_{1'0}-t_{1's}|$ shown in FIG. $21c_4$ is finally obtained as shown in FIG. $21c_3$. A decision of a fillet shape can be made on the basis of this result.

An embodiment of a simplified deciding method will be further described.

When a difference between a pattern having a solder joint with a good fillet shape as shown in FIG. $21b_1$ and a pattern having a solder joint of an object to be inspected shown in FIG. $21b_2$ is obtained, it results as shown in FIG. $21b_3$. The thus obtained pattern is similar in shape to that shown in FIG. $21c_4$. In this case, it is not at all necessary to compare them one by one with that of a solderless joint, and therefore, the decision of a fillet shape is materially simplified.

In the aforementioned figures, the symbols used are as follows:

The solder thickness of a solder joint of an object to be inspected: $t_{1'0}$ is given by $t_{1'0}=(\ln I_2 - \ln I_{1'0})/\mu_1$ The solder thickness of a good solder joint: $t_{1's}$ is given by:

$t_{1's}=(\ln I_2 - \ln I_{1's})/\mu_1$

Accordingly, in this case, $|t_{1'0}-t_{1's}|=|(\ln I_{1's}-\ln I_{1'0})|/\mu_1$ where $I_2$: Transmitted X-ray dosage of the joint lead
$I_{1'0}$: Transmitted X-ray dosage of solder joints of an object to be inspected
$I_s$: Transmitted X-ray dosage of a good solder joint
$\mu_1$: X-ray absorption coefficient of solder The above description can be replaced by the following description.

In the decision of a fillet shape, a difference between an inspected fillet waveform and a good fillet waveform is obtained.

$$\Sigma |F-F_0| = \Sigma |\bar{f}-f-(\bar{f}-f_0)| \quad (8)$$
$$= \Sigma |f-f_0|$$

where F: fillet shape to be inspected, f: detection waveform, $F_0$: good fillet waveform, $f_0$: good detection waveform, $\bar{f}$: waveform of fillet without solder Therefore, the decision can be accomplished without using an image of a solderless fillet.

Even though the overall soldering state is the same, there are a variety of good products due to unevenness of a supply of solder, slight deviation of leads and the like. There are also a variety of shape of waveform signals in the X-ray image. It is therefore effective that a plurality of good waveforms corresponding to a variation of soldering, a good waveform by which the value of Equation (8) is minimum is obtained, and the quality is decided from the value.

In the embodiment of the present invention, a number of good waveforms are collected. Fillet waveforms $GW_1$ to $GW_M$ of a number of good products are subjected to clustering, those similar in shape are collected, the overall good waveform is divided into a few classes, and a typical good waveform is automatically extracted for every class. The algorithm of clustering includes a so-called K average algorithm. A system for automatically extracting a good waveform by use of the aforesaid algorithm is described below.

In FIG. 22, $WM_1 - WM_R$ designate means for averaging waveforms, $S_1 - S_N$ reference waveforms for decision, W a detection fillet shape obtained by the reference waveforms $S_1 - S_N$, and min $|W-S_j| \geq \epsilon (j=1$ to $N)$ a defect decision condition with $\epsilon$ as the decisional threshold.

K average algorithm: First, n number of good waveforms are divided into K classes. The following steps are then carried out.

Step 1: $Zj(1)$ $(j=1, 2, \ldots k)$ is used as the center of K number of initial clusters, K number is suitably selected from good waveforms $X_i$ $(i-1, 2, \ldots n)$.

Step 2: Xi is compared with Zj(k) $(k-1, 2, \ldots)$ to search for the most similar Zj(k). n number of good wave forms Xi are divided into K number of classes.

Step 3: The operation of the following equation is effected so that the sum of differences between all Xi belonging to Zj(k) and the cluster center is minimum. The cluster center is then changes to Zj(k+1). (The waveform average is effected by $WM_1$ to $WM_R$ as shown in FIG. 22.)

$$Zj(k+1)=(\Sigma Xi)/Nj$$

$$xi \epsilon Zj(k)$$

where, Nj: number of X1 belonging to Zj(k)

Step 4: With respect to all j, the step is returned to Step 2 until Zj(k+1)=Zj(k) is established. If established, Zj(k) is taken as a good waveform.

The method for selecting waveforms by use of the K average algorithm is carried out for every part or every specific solder joint to thereby obtain good waveforms $(S_1 - S_n)$ as decisional reference datum.

In order to cope with the variation of soldering, it is important to collect good waveforms of not only a single printed circuit board but a number of printed circuit boards. The collection of good waveforms and the selection of the reference good waveform are shown by the flowchart of FIG. 23. As shown in FIG. 23, a position of a solder joint is extracted from the X-ray image similar to the inspection extraction position. A waveform signal of the solder joint is inputted into the CPU 8 on the basis of the obtained result. These waveforms are sequentially stored in the memory. After a predetermined number of waveforms have been collected, good waveforms are selected by the clustering method described above.

While in the foregoing, data to be collected has been increased with respect to the variation of a number of soldering, it is to be noted that a variation is prepared artificially such that a supply of solder is changed or a part is placed being slightly deviated, and a detected waveform of the solder joint may be used as a reference.

Furthermore, while in the foregoing, the one surface mounted substrate has been used, it is to be noted that an image of a solder joint is detected so that a substrate is tilted as shown in FIG. 25 so that the inside and outside solder joints are not interfering in an overlapping relationship, whereby similar processing can be made for a dual mounted (dual-sided) substrate.

Moreover, while in the foregoing, the fillet decision has been carried out in the lead tip direction, it is to be noted that he decision may be made in the lead row direction on the basis of the position detection of the solder joint.

In addition, instead of comparison with the good fillet waveform, decision can be carried out by analysis of the fillet waveform itself.

Moreover, defects of solder joint include a bridge defect, a solder ball defect and the like, produced between solder joints. In the present invention, a binary image of an X-ray fluoroscopic image is obtained by the binarization circuit 25 shown in FIG. 8, and a binary image is projected in a vertical direction between the solder joints obtained in FIGS. 15 and 17. FIG. 24(a) shows a binary image when a soldering ball and solder bridge is present. FIG. 24(b) shows a projection, and FIG. 24(c) shows a waveform in which the projection is binarized by a threshold level Th3. The CPU 8 receives a projection obtained by the projection generating circuit 26, and after the projection has been binarized, the length of "0" or "low" binary lead, from the end between the solder joints is obtained to decide a defect.

As described above, according to the embodiment of the present invention, the horizontal and vertical projection values are obtained with respect to the X-ray fluoroscopic image of the solder joint whereby the position of the individual solder joint is extracted, and defects such as a insufficient solder, lifted leads, bridge defects, solder ball defects, etc., are determined in accordance with the extracted position. In the future, there is a possibility that the dual-sided mounting as shown in FIG. 25 is often used. In this case, the decision of a deviated lead, bridge and solder ball may be carried out by the aforementioned system, but there is a possibility that the X-ray fluoroscopic images of the inside and outside solders overlap, the dynamic range of detection is short, and the sensitivity of detection of surplus or insufficient solder lowers. As shown in FIG. 25, in such a case, the substrate (printed board) is tilted in the lead row direction, and the inside and outside (top and bottom as viewed in the figure) solder joints are deviated to remove an overlap before detection. FIG. 26 shows an example of the thus detected X-ray fluoroscopic image. FIG. 26(a) shows the case where the dual-side mounted substrate is tilted, and FIG. 26(b) shows the X-ray fluoroscopic image. In the projection (vertical) in the lead tip direction, the FIG. 27 configuration results, and only a set of inside and outside (top and bottom as viewed in the figure) solder joints can be separated in the system shown in FIG. 17. In such a case, a middle point $ic_n$ and $ie_n$ is obtained as shown in FIG. 27 whereby the inside and outside may be separated to evaluate the amount of solder present for each. If the extraction of each fillet shape is carried out at each center portion of $is_n$ to $ic_n$ to $is_n$, it can be carried out exactly similar to the one surface mounted substrate.

In sum, FIG. 28 shows a flow of image processing when a substrate is not tilted such as the case of one surface (single-surface) mounting (when a substrate is not tilted at $\psi$), FIG. 29 shows a flow of image processing when a substrate is tilted (when a substrate is tilted at $\psi$), and FIG. 30 shows a flow of inspection of a dual mounted (dual-sided) substrate. In FIG. 30, the phase terms $F_1$ and $F_3$ refer to a quadrant (phase) of a lead of a solder joint of an IC (part) 1 to be inspected. In this embodiment, clockwise numbers $F_1$ to $F_4$ are indicated.

Flows of FIGS. 28 and 29 will be explained in connection with the hard structure of FIG. 8. Reference numerals 101, 101' designate the operation of TV camera 6 and A/D converter 11 shown in FIG. 8; 102, 102' the operation of the shading compensation circuit 12; and 103, 103' the operation of the logarithmic conversion circuit 13. The image is inputted into the memory 14 by 103 and 103'. The positions detect of a soldering area 104 and 104' and 105, 105' designate the solder joint extraction processing in which the CPU 8 analyzes the horizontal and vertical projections prepared by 23 and 24. The solder quantity decision and misaligned lead decision 106, 106', and 107 designate the defect decision processing in which the CPU 8 analyzes the vertical projection prepared by the vertical projection generating circuit 24. Bridge decision 108 designates the defect decision processing in which the CPU 8 analyzes the projection prepared by the projection generating circuit 26. Fillet shape decisions 109 and 109 designate the defect decision processing in which the CPU 8 receives the image date from the memory 14 with the position of the solder joint obtained by 104, 105 or 104', 105' used as a reference.

The inspection flow of FIG. 30 will be described in connection with the whole structure of FIG. 1. In 110, the CPU 8 actuates the $\psi$ stage 7 through the stage control unit 9. In 111, the CPU 8 actuates the XY$\theta$ stage 3 through stage control unit 9. Step 112 indicates the processing operation shown in FIG. 28, which is carried out by the CPU 8 and the picture processing unit 10 shown in FIG. 1. Step 113 designates a process carried out by the CPU 8. Step 114 designates the process in which the CPU 8 actuates the $\psi$ stage 7 through the stage control unit 9. Step 116 designates the process shown in FIG. 29 which is carried out by 8 and 10. Process step 117 designates a process carried out by the CPU 8. Step 118 denotes the process in which the CPU 8 actuates the stage 3 through the stage control unit 9. Steps 119 and 120 designate the same process as that of 115 and 116. Step 121 designates a process carried out by the CPU 8. Steps 122 and 123 designate the process in which the step is returned to the original state upon completion of inspection, in which operation, the stages 3 and 7 are actuated by the CPU 8.

While in the present embodiment, a soldering image is used as a position of a solder joint, it is to be noted that a lead frame of a part or a target mark provided on the lead frame may be used for the imaging datum point.

While in the present embodiment, since a substrate is tilted, the $\psi$ stage 7 is relatively used. It is to be noted that a stage on which a substrate (printed board) 2 is placed may be made to possess the tilting function or remain fixed while only the image intensifier 5 and TV camera 6 are moved as shown in FIGS. 32 and 33.

In the above-described embodiment, in the dual mounted substrate, the substrate is tilted so that the inside and outside (top and bottom) solder joint image projections do not overlap. However, alternatively, as shown in FIG. 58, a position at which parts 1 such as ICs are placed on the inside and outside of the substrate 2, top and bottom as viewed in the figure, is deviated by a ½ pitch portion of the spacing P between the leads, that is P/2. The parts are mounted whereby the inside and outside solder joints can be separated and detected without tilting the substrate.

It is known that if the X-ray is large in amount of irradiation, an element such as an IC may be damaged. In the embodiment of the present invention, as shown in FIG. 34, a shutter 301 is provided so that the X-ray solely irradiates the IC part 1 during inspection. A filter 311 is provided to filter the X-ray on the solder joint. The shutter 301 is formed of Pb having a thickness of approximately 1 mm, and the filter 311 is formed of Cu having a thickness of approximately 0.1 to 0.2 mm. The filter 311 can reduce the damage to the element without affecting the solder imaging in order to reduce a proportion of a long portion of a waveform of the X-ray. In order to reduce damage to the element, there can be provided an X-ray shield plate in the state wherein mask patterns for shielding the X-ray are superimposed on the portion of the element or on the part itself.

While in the present embodiment, the image intensifier and the TV camera have been used as an X-ray detector, it is needless to say that a configuration of using a fluorescent plate, a high sensitive camera and an X-ray TV camera may be employed.

As described above, according to the present embodiment, it is possible to automatically extract a position of a solder joint from an X-ray transmitted image signal and to automatically inspect for solder joint defects.

Next, an embodiment of the present invention will be described hereinafter with reference to FIG. 3(d), FIG. 4(b) and FIGS. 35 to 44.

Figure 3A:
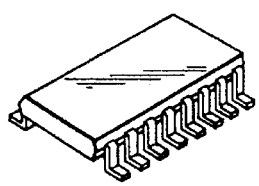
FIG. 3 is a view showing the possible forms of ICs mounted on the substrate.
Figure 3B:
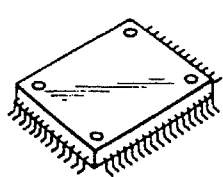
Figure 3C:
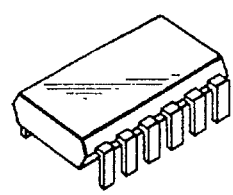
Figure 3D:
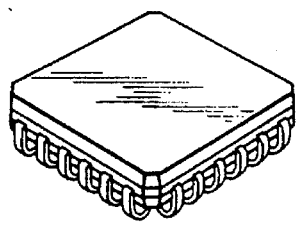
Figure 3E:
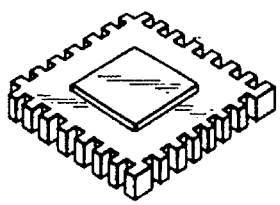
Figure 4A:
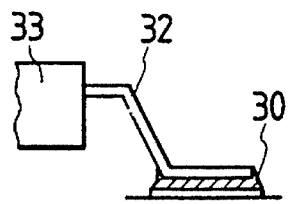
FIG. 4 is a partial side view showing the state in which various ICs are bonded by solder.
Figure 4B:
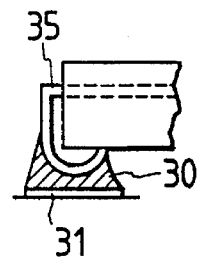
Figure 4C:
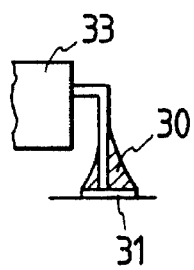
Figure 4D:
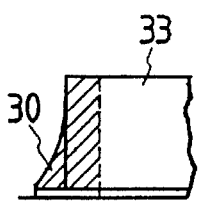

FIG. 3(d) shows an example of an surface mounted part as an inspection object of the present invention. FIG. 4(b) shows a sectional shape of an IC part in the soldered state. FIG. 35 shows an example of an X-ray image by which a solder joint of such a part is detected. An IC lead image 132 within a part package along with the lead 32 of a part of solders 131a and 131b on the substrate pad are similarly overlapped and detected. Reference numerals 133 and 134 designate an example of bridge defects, and 135 an example of a solder ball defect. In the case where a defect such as a fine soldering bridge as shown at 133 occurs in an area detected while being overlapped with a lead, the bridge image is mixed with the lead image, and therefore, it is difficult to discriminate and decide the bridge with high accuracy. The present invention provides a method for the decision to solve the aforesaid problem, which will be described in detail by use of a solder bridge defect example.

The formation of the X-ray fluoroscopic image in the J lead is as previously mentioned as shown in FIG. 4(b), FIGS. 8 to 10, and FIGS. 12a to FIG. 17.

A method for deciding a soldering bridge defect according to the present invention executed by the CPU using an image of a solder joint of a lead detected, as shown in FIG. 35, will be described hereinafter. In accordance with the positional coordinate of each lead obtained as described above, as shown in FIG. 36, an area is divided, between the leads, into (A) an area in which no lead image is present, (B) an area in which a pattern image LF of a lead is detected, and (C) an area in which a flat plate-like lead image PF is detected, these areas being separated from the background of a substrate, a lead image or the like in each area. A threshold is set to the highest level in the range in which only a soldering bridge (of which absorption relative to the X-ray is smaller than a lead) 51 to 53 are present. In FIG. 36, an image signal at a position shown at arrow AR is one shown in FIG. 37.

In FIGS. 36 and 37, PF is a flat plate-like lead portion, and LP is a lead pattern portion. In FIG. 37, S51, S52 and S53 are bridge image signals produced by solder bridges 51, 52 and 53, respectively. As will be apparent from these figures, if in the areas (A), (B) and (C), $V_A$, $V_B$ and $V_C$ are used to obtain the binary image. An image signal (FIG. 38) separated from the background to actualize only a bridge defect is obtained in each area. That is, according to the present method, in the areas (A), (B) and (C), a binary image in which soldering bridges 53 and 51 are completely actualized is obtained, and a bridge decision is carried out using the binary image.

A method for the decision will be described with reference to FIGS. 39a to 39c by way of an example of processing in the area (A).

First, in the binary image caused by the image $V_A$ shown in FIG. 39a, a distribution (FIG. 39b) in the direction of X of the number of picture elements of a portion with no solder in the case of counting in the direction of Y is obtained to calculate a bridge detection value (FIG. 39c) corresponding to the range of less (YA−ΔY) with respect to the length YA in the direction of Y of the processing area. Next, the width Xl in the direction of X is obtained as a bridge length, and when a difference between said width and the width XA in the direction of X of the processing area is smaller than a predetermined value ε (condition XA−Xl≦Xε), the presence of bridge is detected. In the FIG. 39c example, XA−Xl=0 results, and the presence of bridge can be decided. For the bridge 51 in the area (C), similar effect is obtained. In the decision area (B), as shown in an example of FIG. 36, in the case where a soldering bridge 52 lower in contrast than the image of the lead 32 is present, as shown in FIGS. 40a to 40c a soldering bridge image of portion superimposed on the image of the lead 32 can be placed in good shape but a soldering bridge image produced at a position not superimposed to the lead 32 cannot be detected. Accordingly, it is not reflected upon a bridge obtained in FIG. 40c, and sufficient detection accuracy cannot be obtained.

In the present embodiment, for the area (B) shown in FIG. 41 in which a pattern image 50 of the lead 32 is detected, a bridge decision according to the method which will be described later is carried out. As shown at an image signal level (axis X) in FIG. 41, two thresholds Vh and Vl are used for the area (B) to prepare two kinds of binary images. That is, Vh is a threshold level at which a lead portion is separated from a printed circuit board 2 to place it in good shape, and Vl is the same level as VB explained in FIG. 37, that is Vl=VB, which is the maximum of the range in which the lead 32 is not detected. FIGS. 42a to 42d show examples of the aforesaid two kinds of binary images with respect to the area (B) in the FIG. 36 example.

Figure 42A:
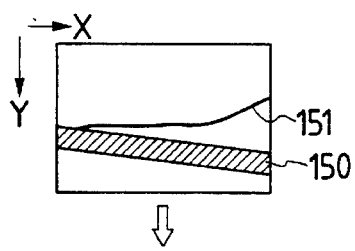
Figure 42B:
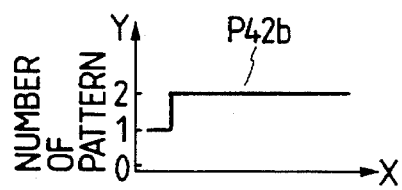
Figure 43B:
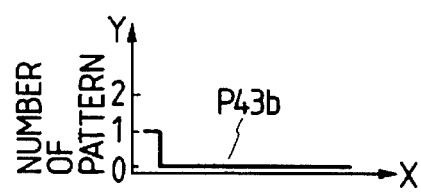
Figure 43C:
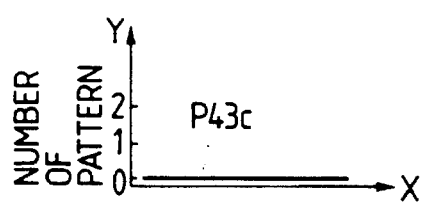

In the present embodiment, pattern number distributions (Y axis direction) in which the number of patterns when searched in the direction of axis Y are counted for every picture element of each coordinate X as shown in FIGS. 42b and 43b (the distributions being indicated at P42b and P43b). These are compared with reference pattern number distribution (indicated at P42c and P43c in FIGS. 42c and 43c) likewise obtained in advance using a good sample, to obtain a difference therebetween, the result of which is shown at (P42b−P42c) and (P43b−P43c) in FIGS. 42d and 43d, respectively.

The presence of a bridge defect is decided is decided for those in which either of the aforesaid calculations result in a difference. Reference numeral 151 of FIG. 42a and 152 of FIG. 43a denote a bridge, and 150 denotes a pattern of a lead.

Figure 42C:
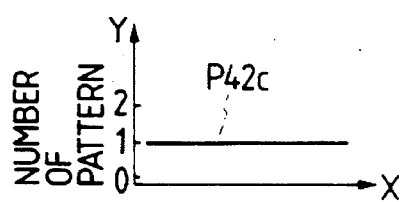
Figure 42D:
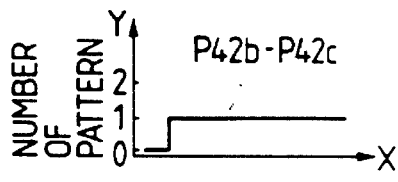
Figure 43D:
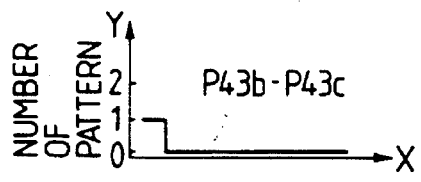

It is understood from the examples of FIGS. 42d and 43d that in both the results for decision of images, a difference is recognized and the bridge detection decision is made. If a method for ignoring a difference of a fine width is employed for the results of (P42b−P42c) and (P43b−P43c), it is possible to remove an erroneous decision affected by noises or the like.

While in the foregoing, a description has been made using an example of a solder bridge defect, it is noted that according to the present invention, a defect of a solder ball or the like can be likewise detected.

The present embodiment can be also applied to an inspection of a soldering bridge on a substrate 2 as shown in FIG. 44 in which parts 1 having a J lead 32 are mounted on both surfaces. In such a mounted substrate, the parts 1 having the inside and outside J leads are mounted substantially at the same position but on opposite sides of the substrate. Therefore, the image detected and processed by the method shown in FIG. 1 is as shown in the example of FIG. 45. In the Figure, reference numeral 32 designates a lead, 42 a soldering bridge and 131 the other lead, respectively.

Accordingly, if a portion between leads is divided into decision areas (A), (B) and (C) corresponding to the position of the image of the lead 32 in a manner similar to the method shown in FIG. 36, in the area (A) in which the image of the lead 32 is not present and the area (C) in which the image of the flat plate-like lead 32 is detected, the bridge decision can be made by using the method similar to those shown in FIGS. 39 (1a) to (3a). However, in the area (B), as shown in FIG. 45, a portion in which a pattern image of the lead 32 among the inside and outside ICs is superimposed and portions not superimposed occur due to the slight misalignment of the position of the inside and outside J lead parts 1. Therefore, the image signal waveform of the portion as indicated by the arrow in FIG. 45 is as shown in FIG. 46. In the embodiment, three thresholds Vh, Vm and Vl are provided. The Vh is a level in which images of all the leads 32 detected at a darker level (low image signal level) than a level (material level) 60 of the printed circuit board 2 can be separated from the material and actualized in the area (B). The Vm is a level in which a superimposed portion of the inside and outside leads can be actualized. The Vl is a level in which an image at a darker level than superimposed portions 61 and 62 of the lead can be actualized.

Figure 47A:
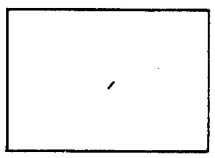
Figure 48A:
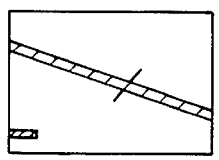
Figure 49A:
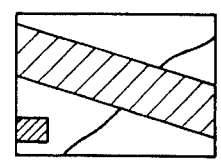
Figure 47B:
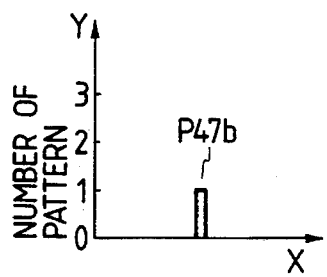
Figure 48B:
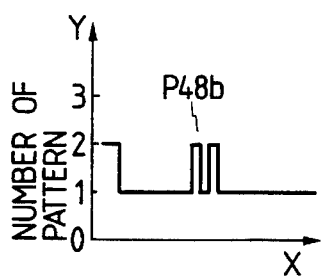
Figure 49B:
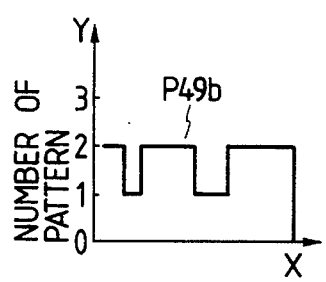
Figure 47C:
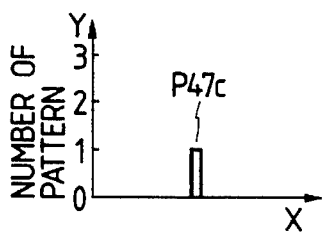
Figure 48C:
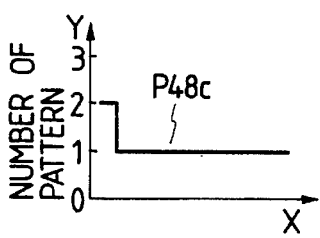
Figure 49C:
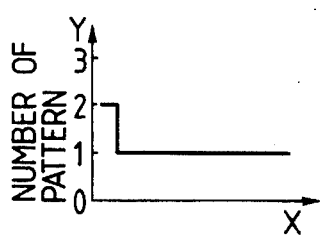
Figure 47D:
Figure 48D:
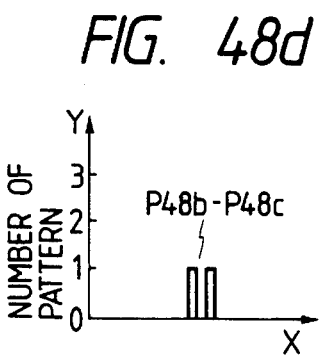
Figure 49D:
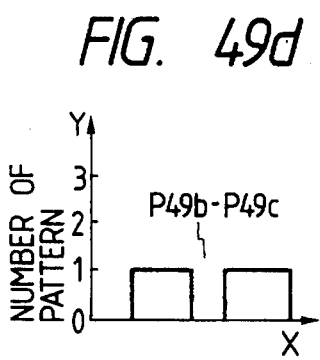

When binarized images are prepared from the Vh, Vm and V↓ in the region (B), they are as shown in the examples of FIGS. 47a, 48a and 49a. With respect to the respective images, pattern number distributions P47b, P48b and P49b when searched in the direction of Y are obtained in a manner similar to the method shown in FIGS. 42a to 42d and 43a to 43d, and these are compared with the pattern number distributions P47c, P48c and P49c obtained in advance in a manner similar to the former with respect to good product reference to obtain differences P47b–P47c, P48b–P48c and P49b–P49c. If any difference is recognized, the bridge can be decided, enabling realization of inspection with high accuracy.

In the case of this example, all the results have a difference, thus rendering inspection of bridge possible. Alternatively, if a good reference pattern is stored in advance as a binary image, and if an image obtained form a difference between the reference pattern image, the image of FIG. 47a and the image of FIG. 48a is obtained, the bridge can be actualized. It is possible to decide a bridge by the method shown in FIGS. 39a to 39c and 40a to 40c using the aforesaid image obtained from the difference.

As described above, according to the present embodiment, in inspection the soldering of the mounted part using the X-ray as an inspecting means, influences from the lead image of the IC part of the like can be removed. Therefore, high detection performance even with respect to ta fine soldering bridge produced between the part leads can be obtained.

Another embodiment of the present invention will be described hereinafter.

FIG. 3 shows an example of a surface mounted part as an inspection object of the present embodiment. FIG. 4 shows a cross-sectional shape of IC in the soldered state.

FIGS. 50a to 50c show an example of an X-ray image in which a solder joint of such a part is detected. Particularly, an example of a J lead will be described. FIG. 50a shows an example of an image of a series of normal solder joints, in which part leads 35 and pads 31 on the circuit board are superimposed and detected. FIG. 50b shows an example of an X-ray image in the case where a defect in misalignment of position at which IC is mounted occurs. FIG. 50c shows an example of an X-ray image in the case where a bent lead defect 60 occurs. The formation of an X-ray fluoroscopic image in the J lead is as described previously.

For the X-ray fluoroscopic image of the J lead obtained in the manner as described above, the picture processing unit is used to obtain a horizontal projection j in an area as shown in FIG. 51a.

A calculation equation for a horizontal projection H(j) with respect to an image f(i,j) is given below.

$$H(j) = \sum_{i=i_1}^{i_2} f(i,j) \quad (9)$$

As the result, the horizontal projection H(j) as shown in FIG. 51b is obtained. The CPU 8 receives H(j) to obtain points of intersection js and je with the threshold $Th_1$ and the horizontal projection H(j) as shown in FIG. 52, which are used as positions of the vertical solder joints. Here, the threshold $Th_1$ is set in advance, or a value is used which is subjected to internal division at a ratio set in advance by the maximum and minimum of the inputted horizontal projection H(j).

Next, areas $jp_1$ and $jp_2$ moved through a predetermined amount with respect to js and je as shown in FIG. 53a are calculated, and a vertical projection V(i) in the areas $jp_1$ to $jp_2$ is obtained using the picture processing unit 10. The $jp_1$ to $jp_2$ correspond to the area in which a part of a pad of a solder joint to be detected externally of the lead tip portion is present and can be obtained, for example, by the following equations:

$$jp_1 = \frac{1}{2}(js+je)-\Delta j_1$$

$$jp_2 = \frac{1}{2}(js+je)-\Delta j_2 \quad (10)$$

The method for calculation of the vertical projection V(i) is expressed by the following formula.

$$V(i) = \sum_{j=jp_1}^{jp_2} f(i,j) \quad (11)$$

An example of V(i) obtained is shown in FIG. 53b. The CPU receives V(i) to obtain points of intersection $is_1$, $ie_1$ to $is_4$, $ie_4$ between the threshold $Th_2$ and V(i), which use as positions of vertical pad. This is similar to the setting of the threshold $Th_2$.

In the CPU 8, a misalignment decision area 235 is provided between pads as shown in FIG. 55a with the pad positions js, je, and $is_1$, $ie_1$ to $is_4$, $ie_4$ obtained as described above used as a reference. This area may be set as follows, for example.

$$ja=js+A, \ jb=je+B$$

$$ia_1=\frac{1}{4}(is_1-ie_1+is_2+ie_2)-\frac{1}{2}D_w$$

$$ib_1=\frac{1}{4}(is_1-ie_1+is_2+ie_3)-\frac{1}{2}D_w$$

where $D_w$ represents the decision area width.

Next, as shown in FIG. 55b, an image within each decision area 235 is binarized in the picture processing unit 10 to obtain a vertical projection value of a binary image. With respect to the waveform as in FIG. 55c obtained from the aforesaid projection value, waveform widths $\Delta W_1$ to $\Delta W_4$ crossed with a reference level $V_w$ set to the CPU 8 are calculated by the CPU 8, and when the waveform widths are larger than a predetermined allowable value, a misaligned lead is decided.

Also, in the case where the printed circuit board 2 a an object to be inspected is a dual mounted substrate as shown in FIG. 44, an X-ray image obtained by the detection method as shown in FIG. 12 is detected as a single image in which the inside and outside substrate pads are superimposed. A normal lead as well as the inside and outside leads are detected in a superimposed mode as shown in FIG. 50a, and in case where a misalignment of at least one lead is present, an image forced out between the pads can be detected as shown in FIG. 50b and 50c. Therefore, the decision of the misalignment in position of lead can be executed similarly to the aforementioned dual mounted substrate.

FIG. 56 shows another embodiment for obtaining a setting position of a misaligned lead decision area provided between the substrate pads. Reference patterns 41 and 42 for recognition of position are provided in advance in a vacant space on the printed circuit board 2 as shown in FIG. 56. In the step of coating a solder paste when the circuit board is assembled, the solder is also coated on the reference patterns 41 and 42 for recognition of position so as to obtain a high contrast image when the X-ray image is detected. Reference numeral 45 designates a through hole.

At the time of decision of a misaligned lead, horizontal and vertical projections Hm(j) and Vm(i) are obtained in connection with each reference pattern 49 for recognition of position as shown in FIG. 57 to calculate points of intersection $jm_1$, $jm_2$, $im_1$, and $im_2$ with predetermined thresholds $V_{TH3}$ and $V_{TH4}$ by the CPU 8. After this calculation has been done in connection with the position recognition reference patterns 41 and 42, the relative position coordinate value between the position recognition reference patterns 41 and 42 inputted into the CPU in advance and the value of the pad dimension are used to set a misaligned lead decision area between the pads.

In another method, as shown at 43 and 44 in FIG. 56, a position recognition reference pattern is provided at a position close to a substrate pad 48 to set a misaligned lead decision area in a method similar to the method formerly discussed. In the third method, as shown at 45 in FIG. 56, a clearance pattern by which a particularly high contrast image is obtained is used as a reference to set a misaligned lead decision area. Even if this method is used, a misaligned lead decision area can be set in a method similarly when the aforesaid position recognition reference pattern is applied.

As described above, according to the present invention, in inspecting a soldering of a mounted part by use of the X-ray as detection means, it is possible to detect an amount of a misaligned position of leads with respect to the substrate pad with high accuracy.

FIG. 58 is a view showing a construction of mounting electronic parts onto a substrate to which the inspection method of the present invention as described above can be easily applied. Solder joints 30 provided on leads 235, 236, . . . 23n and 235', 236', . . . 23n' provided on the opposite sides of the substrate 2 are arranged with a pitch P, and arranged with a pitch deviated by P/2 one to the other so that the X-ray transmitted images from one side of the substrate 2 are not superimposed between the images on the opposite sides.

The thus structured electronic-part mounting construction is an apparatus provided with an effective construction in that the aforementioned inspection according to the present invention can be carried out by simple means without tilting the substrate.

We claim:

1. A method, for use with an X-ray fluoroscopic imaging apparatus, of inspecting a solder joint, the method comprising the steps of:

obtaining an X-ray fluoroscopic image signal by irradiating an X-ray on an object to be inspected, the object being located by a specimen stage and formed by soldering a lead of an electronic part to a substrate at said solder joint;

extracting a position of the solder joint as the object to be inspected from said obtained X-ray fluoroscopic image signal;

defining, from the X-ray fluoroscopic image signal, a plurality of inspection areas on a solder portion and a peripheral portion of the solder joint in accordance with the extracted position of said solder joint; and, detecting a defect with respect to the solder joint in accordance with a min $|W-S_j|$ ($j=1 \ldots N$) of an integrated value $|W-S_j|$ of differential images between an X-ray fluoroscopic image signal shape W obtained from said defined inspection area of said solder portion of the solder joint and a plurality of reference image signal shapes $S_j$ ($j=1 \ldots N$) designated as a typical good solder joint by comparing said X-ray fluoroscopic image signal shape W with said plurality of reference image signal shapes $S_j$ ($j=1 \ldots N$) designated as the typical good solder joint obtained by measuring an X-ray fluoroscopic image signal shape for the typical good solder joint, for every said defined inspection area of said solder portion, and detecting a defect between the solder joints in accordance with an X-ray fluoroscopic image signal obtained from said defined inspection area of said peripheral portion of the solder joint for every said defined inspection area of said peripheral portion.

2. The method according to claim 1 wherein the extracting step includes extracting said position of the solder joint by extracting i) a position of a lead substantially along a longitudinal direction by a first projection distribution, wherein the first projection distribution is a first intensity distribution of said x-ray fluoroscopic image signal transmitted through said object in a first direction substantially orthogonal to said longitudinal direction and ii) a position of a lead in said first direction by a second projection distribution, wherein the second projection distribution is a second intensity distribution of said x-ray fluoroscopic image signal transmitted through said object in said longitudinal direction.

3. The method according to claim 1 wherein the step of detecting includes evaluating by comparing at least one of a width and a spacing of the solder joint detected from said x-ray fluoroscopic image signal of each of the inspection areas, with a reference value.

4. The method according to claim 1 wherein the detecting step includes evaluating an amount of solder at each of a plurality of solder joints by integrating the x-ray fluoroscopic image signal of each of said inspection areas.

5. The method according to claim 1 wherein the comparing step includes comparing a number of patterns of a binary image signal and binary image signals of a good solder joint.

6. The method for inspecting solder joints according to claim 1 further comprising the steps of:

obtaining the first X-ray fluoroscopic image by irradiating an X-ray on a second object to be inspected which second object is located by said specimen stage and which the second object is mounted by soldered leads on both surfaces of a substrate, the substrate and X-ray being angled in relationship to each other so as to obtain said first X-ray fluoroscopic image of both an inside solder joint on a first side of the substrate and an outside solder joint on a second side of the substrate without superposition of said inside and outside solder joints;

detecting defects of solder quantity and fillet shape on both of the inside solder joint and the outside solder joint by evaluating said first X-ray fluoroscopic image;

obtaining a second X-ray fluoroscopic image by irradiating said X-ray on said second object to be inspected in a state whereat said X-ray irradiates said substrate and said second object substantially perpendicular to a plane defined by said substrate; and, detecting a defect of a misaligned lead and a bridge on both of the inside solder joint and the outside solder joint by evaluating said second X-ray fluoroscopic image.

7. The method according to claim 1, further comprising obtaining said plurality of reference image signal shapes of good solder joints from an X-ray fluoroscopic image signal of a typical good solder joint.

8. The method according to claim 7, further comprising obtaining the X-ray fluoroscopic image signal of said typical good solder joints by clustering signals of good solder joints with respect to X-ray fluoroscopic images of a number of good solder joints according to a K average algorithm.

9. The method for inspecting a solder joint by an X-ray fluoroscopic image according to claim 7, further comprising preparing the X-ray fluoroscopic image of said typical good solder joint by varying soldering conditions.

10. An apparatus for inspecting solder joints on a substrate and areas between solder joints using X-ray fluoroscopic imaging, the apparatus comprising:

irradiating means for irradiating an X-ray generated from an X-ray source;

a specimen stage for locating an object to be inspected, the object having a lead of an electronic part soldered to a substrate;

an X-ray detector for detecting an X-ray fluoroscopic image signal obtained by transmitting said X-ray through solder joints of the object located by said specimen stage;

solder-joint position extracting means for extracting a position of each of the solder joints of said object to be inspected in accordance with said X-ray fluoroscopic image signal detected by said X-ray detector;

inspection-area setting means for defining a plurality of inspection areas on each of i) a portion of a solder joint and ii) a peripheral portion of a solder joint, corresponding to each of the solder joints in accordance with the extracted position of each solder joint extracted by said solder joint position extracting means;

preparing means for preparing a plurality of reference image signal shapes $S_j$ (j=1 ... N) designated as typical good solder joints by measuring X-ray fluoroscopic image signal shapes for typical good solder joints in accordance with said X-ray fluoroscopic image signal detected by said X-ray detector;

defect detection means for i) detecting a defect with respect to the solder joints in accordance with a degree of coincidence between an X-ray fluoroscopic image signal shape W obtained from said defined inspection area of said solder portion of the solder joint and a reference image signal shape S of a good solder joint by comparing said X-ray fluoroscopic image signal shape with said reference image signal shape of said good solder joint obtained by measuring the X-ray fluoroscopic image signal shape for said good solder joint for every said defined inspection area of said solder portion, and ii) detecting a defect between the solder joints in accordance with an X-ray fluoroscopic image signal obtained from said defined inspection area of said peripheral portion of the solder joint for every said defined inspection area of said peripheral portion; and, wherein, the defect detecting means includes second means for judging a defect of each of the solder joints by comparing the x-ray fluoroscopic image signal shape W of each of the inspection areas set, obtained from the X-ray fluoroscopic image signal detected by said X-ray detector, with the prepared reference image signal shape S of good solder joint, the second means including means for deciding between X-ray fluoroscopic image signal shapes and the prepared reference image signal shapes by a min $|W-S_j|$ (j=1 ... N) of an integrated value $|W-S_j|$ of differential images.

11. The apparatus according to claim 10, wherein:

said solder joints are linearly arranged on said object, said linearly arranged solder joints defining a lead row direction; and, said solder joint position extracting means includes means for i) extracting a position of a lead in a substantially longitudinal direction by analyzing a first projection distribution, wherein the first projection distribution is a first intensity distribution of said x-ray fluoroscopic image signal transmitted through said object in said lead row direction and ii) extracting a position of said lead in said lead row direction by analyzing a second projection distribution, wherein the second projection distribution is a second intensity distribution of said x-ray fluoroscopic image signal transmitted through said object in said substantially longitudinal direction.

12. The apparatus according to claim 10 further comprising binary signal comparison means for comparing respective numbers of binary patterns between a binary image signal of said X-ray fluoroscopic image signal shape obtained from said defined inspection area of said solder portion of the solder joint and a binary image signal of a predetermined good solder joint.

13. The apparatus according to claim 10 further including means for forming said plurality of reference image signal shapes using a typical X-ray fluoroscopic image obtained from a typical good solder joint.

14. The apparatus according to claim 13 including means for forming said typical X-ray fluoroscopic image by clustering a plurality of good X-ray fluoroscopic images obtained from good solder joints according to a K average algorithm.

15. The apparatus according to claim 13 including means for forming said typical X-ray fluoroscopic image by good X-ray fluoroscopic images obtained from good solder joints prepared by varying the solder condition.

16. The apparatus for inspecting solder joints according to claim 10 further comprising:

means for irradiating an X-ray generated from an X-ray source;

a specimen stage for locating an object to be inspected having leads of electronic parts soldered on both surfaces of a substrate so as to form inside solder joints and outside solder joints respectively;

an X-ray detector for detecting a first X-ray fluoroscopic image signal obtained by transmitting said X-ray through the inside solder joints and the outside solder joints of the object located by said specimen stage;

tilting means for tilting at least one of said X-ray and said object so as to obtain a second X-ray fluoroscopic image signal of both of the inside solder joints and the outside solder joints without superposing said X-ray fluoroscopic image signals; and, defect detecting means for judging a defect of solder quantity and fillet shape on both the inside solder joints and the outside solder joints by evaluating said second X-ray fluoroscopic image detected by said X-ray detector when one of the X-ray and object are tilted, and for judging a defect of a misaligned lead and bridge on both the inside solder joints and the outside solder joints by evaluating said first X-ray fluoroscopic image detected by said X-ray detector in the state not relatively tilted.

17. The apparatus according to claim 10, wherein said defect detection means includes means for comparing a width of a solder joint spacing with a reference value.

18. The apparatus according to claim 10, wherein said defect detection means further comprises integrating means for detecting an amount of solder by integration of said X-ray fluoroscopic image signal.

19. The apparatus according to claim 10, wherein said defect judging means includes first means for judging a bridge defect between each of the solder joints by evaluating each of the inspection areas set between each of the solder joints obtained from the X-ray fluoroscopic image signal.

20. The apparatus according to claim 19 wherein said first means includes means for converting the X-ray fluoroscopic image signal to a binary image and for judging defects between each of the solder joints by evaluating a binary image of each of the inspection areas sen between each of the solder joints obtained from the binary image.

21. The apparatus according to claim 19, wherein said defect detection means further comprises binary projection means for effecting a defect detection by projection of said binary image in a longitudinal direction along the electronic part.

22. The apparatus according to claim 10, wherein said X-ray detector further comprises means for obtaining an X-ray fluoroscopic image signal so that inside and outside solder joints of electrical parts mounted on both surfaces of said substrate respectively thereof are not superimposed.

23. The apparatus according to claim 22, wherein said inspection area setting means comprises means for collectively setting a set of inside and outside solder joints as an inspection area.

24. The apparatus according to claim 23, wherein said inspection area setting means further comprises means for dividing a solder joint image into two parts to separate the inside and outside solder joints.

25. The apparatus according to claim 10, wherein said defect detection means comprises subtracting means for subtracting an X-ray fluoroscopic image signal of a solder joint in a first portion from an X-ray fluoroscopic image signal of a joint having no solder in the first portion to thereby extract a soldering fillet shape and effect defect detection by said extracted fillet shape.

26. The apparatus according to claim 10 further comprising rotate means for rotating the optical axes of said X-ray source and said X-ray detector to relatively tilt said object to be inspected.

27. The apparatus according to claim 10, wherein said X-ray detector comprises tilt means for relatively tilting said object to be inspected.

28. The apparatus according to claim 10 further comprising shield means for reducing X-ray damage to the object.

29. An apparatus for inspecting a first solder joint and an area between a plurality of solder joints using X-ray fluoroscopic imaging, the apparatus comprising:

irradiating means for irradiating an X-ray on an object to be inspected to obtain an X-ray fluoroscopic image signal of the object, the object being located by a specimen stage and formed by a lead of an electronic part soldered to a substrate at the first solder joint;

extracting means for extracting a position of the first solder joint as the object to be inspected from said obtained X-ray fluoroscopic image signal;

defining means for defining, from the X-ray fluoroscopic image signal, a plurality of inspection areas on a solder portion of said first solder joint and a peripheral portion of the first solder joint in accordance with the extracted position of said first solder joint;

subtracting means for subtracting an X-ray fluoroscopic image signal shape $I_1$ derived from said X-ray fluoroscopic image signal from an X-ray fluoroscopic image signal shape 12 comprising a state where no solder is present for each of said plurality of inspection areas in accordance with the extracted position to calculate a fillet shape; and, detecting means for i) detecting a defect with respect to the first solder joint in accordance with a minimum of an integrated value of differences between an X-ray fluoroscopic image signal shape obtained from said defined inspection area of said solder portion of the solder joint and a plurality of reference image signal shapes of a good solder joint by comparing said X-ray fluoroscopic image signal shape with said plurality of reference image signal shapes of said good solder joint obtained by measuring the X-ray fluoroscopic image signal shape for said good solder joint for each of said plurality of defined inspection areas of said solder portion of said first solder joint, and ii) detecting a defect between the plurality of solder joints in accordance with an X-ray fluoroscopic image signal obtained from said defined inspection area of said peripheral portion of the first solder joint for each of said plurality of defined inspection areas of said peripheral portion of said first solder joint.

30. A method of inspecting a solder joint in an x-ray fluoroscopic imaging apparatus, the method comprising the steps of:

obtaining an x-ray fluoroscopic image signal by irradiating an x-ray on an object to be inspected, the object being located by a specimen stage of the apparatus and formed by soldering a lead of an electronic part to a substrate at said solder joint;

extracting a position of the solder joint as the object to be inspected from said obtained x-ray fluoroscopic image signal;

defining, from the x-ray fluoroscopic image signal, a plurality of inspection areas on a solder portion of the solder joint in accordance with the extracted position of said solder joint; and, detecting a defect with respect to the solder joint in accordance with a min $|W-S_j|$ ($j=1 \ldots N$) of an integrated value $|W-S_j|$ of differential images between an x-ray fluoroscopic image signal shape W obtained from said defined inspection area of said solder portion of the solder joint and a plurality of reference image signal shapes $S_j$ ($j=1 \ldots N$) designated as a typical good solder joint by comparing said x-ray fluoroscopic image signal shape W with said plurality of reference image signal shapes $S_j$ ($j=1 \ldots N$) designated as the typical good solder joint obtained by measuring an x-ray fluoroscopic image signal shape for the typical good solder joint for every said defined inspection area of said solder portion.

31. The method according to claim 30 wherein:

the step of defining includes defining, from the x-ray fluoroscopic image signal a plurality of second inspection areas on a peripheral portion of the solder joint in accordance with said extracted position of said solder joint; and, the step of detecting includes detecting a defect between the solder joints in accordance with an x-ray fluoroscopic image signal obtained from said plurality of defined second inspection areas of said peripheral portion of the solder joint.

* * * * *

UNITED STATES PATENT AND TRADEMARK OFFICE
CERTIFICATE OF CORRECTION

PATENT NO. : 5,493,594

DATED : February 20, 1996

INVENTOR(S) : Toshimitsu Hamada, et. al.

It is certified that error appears in the above-identified patent and that said Letters Patent is hereby corrected as shown below:

```
Claim 20, column 23, line 27, delete "sen" and insert
therefore --set--.

Claim 29, column 24, line 15, delete "12" and insert
therefore --I₂--.
```

Signed and Sealed this

Twenty-first Day of May, 1996

*Attest:*

BRUCE LEHMAN

*Attesting Officer*  *Commissioner of Patents and Trademarks*